(12) United States Patent
Kratz et al.

(10) Patent No.: US 8,778,914 B2
(45) Date of Patent: Jul. 15, 2014

(54) BISPHOSPHONATE-PRODRUGS

(75) Inventors: Felix Kratz, Ehrenkirchen (DE); Katrin Hochdoerffer, Freiburg (DE)

(73) Assignee: KTB Tumorforschungsgesellschaft mbH, Freiburg Im Breisgau (DE)

( * ) Notice: Subject to any disclaimer, the term of this patent is extended or adjusted under 35 U.S.C. 154(b) by 0 days.

(21) Appl. No.: 13/391,367

(22) PCT Filed: Aug. 24, 2010

(86) PCT No.: PCT/EP2010/005187
§ 371 (c)(1),
(2), (4) Date: Mar. 14, 2012

(87) PCT Pub. No.: WO2011/023367
PCT Pub. Date: Mar. 3, 2011

(65) Prior Publication Data
US 2012/0165296 A1  Jun. 28, 2012

(30) Foreign Application Priority Data
Aug. 25, 2009 (EP) ..................................... 09010871

(51) Int. Cl.
| | | |
|---|---|---|
| *A01N 57/18* | (2006.01) | |
| *A61K 31/66* | (2006.01) | |
| *A61K 38/00* | (2006.01) | |
| *A61K 47/00* | (2006.01) | |
| *A01N 57/00* | (2006.01) | |
| *A01N 43/00* | (2006.01) | |
| *A61K 31/33* | (2006.01) | |
| *A01N 43/42* | (2006.01) | |
| *A61K 31/44* | (2006.01) | |
| *A01N 43/16* | (2006.01) | |
| *A61K 31/35* | (2006.01) | |
| *C07H 15/24* | (2006.01) | |
| *C07H 17/08* | (2006.01) | |
| *C07D 487/00* | (2006.01) | |
| *C07D 491/00* | (2006.01) | |
| *C07D 513/00* | (2006.01) | |
| *C07D 487/14* | (2006.01) | |
| *C07F 9/22* | (2006.01) | |
| *C07F 9/28* | (2006.01) | |

(52) U.S. Cl.
USPC ............. 514/141; 514/1.3; 514/75; 514/102; 514/107; 514/114; 514/120; 514/124; 514/129; 514/183; 514/283; 514/453; 514/455; 536/6.4; 536/6.5; 536/7.1; 540/478; 548/422; 562/21

(58) Field of Classification Search
None
See application file for complete search history.

(56) References Cited

U.S. PATENT DOCUMENTS

| | | | | |
|---|---|---|---|---|
| 6,214,812 B1 * | 4/2001 | Karpeisky et al. | ............... | 514/89 |
| 7,387,771 B1 * | 6/2008 | Kratz | ............... | 424/1.11 |
| 7,445,764 B1 * | 11/2008 | Kratz | ............... | 424/1.69 |
| 7,803,903 B2 * | 9/2010 | Kratz | ............... | 530/328 |
| 7,902,144 B2 * | 3/2011 | Kratz | ............... | 514/15.2 |
| 8,153,581 B2 * | 4/2012 | Kratz | ............... | 514/1.1 |
| 2009/0227544 A1 | 9/2009 | Karpeisky et al. | | |
| 2010/0111866 A1 * | 5/2010 | Kratz | ............... | 424/9.1 |
| 2010/0144647 A1 * | 6/2010 | Kratz et al. | ............... | 514/18 |
| 2010/0311695 A1 * | 12/2010 | Egorov et al. | ............... | 514/107 |
| 2011/0117009 A1 * | 5/2011 | Kratz et al. | ............... | 424/1.11 |
| 2011/0142764 A1 * | 6/2011 | Satchi-Fainaro et al. | ...... | 424/9.1 |
| 2012/0195832 A1 * | 8/2012 | Kratz | ............... | 424/1.65 |

FOREIGN PATENT DOCUMENTS

| | | | | |
|---|---|---|---|---|
| WO | 98/35704 | 8/1998 | | |
| WO | WO 9835704 A1 * | 8/1998 | ............. | A61K 47/48 |
| WO | 2009/083614 A1 | 7/2009 | | |

OTHER PUBLICATIONS

U.S. Appl. No. 13/641,284, filed Apr. 2011, Kratz.*
U.S. Appl. No. 12/964,099, filed Dec. 2010, Raucher et al.*
Erez et al., "Chemotherapeutic bone-targeted bisphosphonate prodrugs with hydrolytic mode of activation," Bioorgan. & Medicinal Chem. Lett. 18:816-820 (2008).*
Segal et al., "Design and development of polymer conjugates as anti-angiogenic agents," Adv. Drug Delivery Rev. 61:1159-1176 (epublished Aug. 20, 2009).*
Engesser, K.H., et al., "Dioxygenolytic Cleavage of Aryl Ether Bonds: 1,10-dihydro-1,10-dihydroxyfluoren-9-one, a novel arene dihydrodiol as evidence for angular dioxygenation of dibenzofuran," FEMS Microbiology Letters, 1989, vol. 65, pp. 205-210.

* cited by examiner

*Primary Examiner* — James H Alstrum Acevedo
*Assistant Examiner* — Thea D' Ambrosio
(74) *Attorney, Agent, or Firm* — McDonnell Boehnen Hulbert & Berghoff LLP

(57) ABSTRACT

The present invention relates to a prodrug, comprising a pharmaceutically and/or diagnostically active compound, and one or more bisphosphonate groups, to a process for producing such a prodrug, and to a pharmaceutical composition comprising said prodrug, to be used for the treatment of bone-related disorders such as bone cancer.

8 Claims, 7 Drawing Sheets

```
                         SEQUENCE LISTING

<160> NUMBER OF SEQ ID NOS: 9

<210> SEQ ID NO 1
<211> LENGTH: 4
<212> TYPE: PRT
<213> ORGANISM: Artificial
<220> FEATURE:
<223> OTHER INFORMATION: cleavable linker sequence

<400> SEQUENCE: 1

Ala Leu Ala Leu
1

<210> SEQ ID NO 2
<211> LENGTH: 6
<212> TYPE: PRT
<213> ORGANISM: Artificial
<220> FEATURE:
<223> OTHER INFORMATION: cleavable linker sequence

<400> SEQUENCE: 2

Ser Ser Tyr Tyr Ser Arg
1               5

<210> SEQ ID NO 3
<211> LENGTH: 8
<212> TYPE: PRT
<213> ORGANISM: Artificial
<220> FEATURE:
<223> OTHER INFORMATION: cleavable linker sequence

<400> SEQUENCE: 3

Phe Pro Lys Phe Phe Ser Arg Gln
1               5

<210> SEQ ID NO 4
<211> LENGTH: 8
<212> TYPE: PRT
<213> ORGANISM: Artificial
<220> FEATURE:
<223> OTHER INFORMATION: cleavable linker sequence
<220> FEATURE:
<221> NAME/KEY: X
<222> LOCATION: (6)..(6)
<223> OTHER INFORMATION: X = Nitrophenylalanine (Nph)

<400> SEQUENCE: 4

Lys Pro Ile Glu Phe Xaa Arg Leu
1               5
```

```
<210> SEQ ID NO 5
<211> LENGTH: 8
<212> TYPE: PRT
<213> ORGANISM: Artificial
<220> FEATURE:
<223> OTHER INFORMATION: cleavable linker sequence

<400> SEQUENCE: 5

Gly Pro Leu Gly Ile Ala Gly Gln
1               5

<210> SEQ ID NO 6
<211> LENGTH: 8
<212> TYPE: PRT
<213> ORGANISM: Artificial
<220> FEATURE:
<223> OTHER INFORMATION: cleavable linker sequence

<400> SEQUENCE: 6

Gly Pro Gln Gly Ile Trp Gly Gln
1               5

<210> SEQ ID NO 7
<211> LENGTH: 4
<212> TYPE: PRT
<213> ORGANISM: Artificial
<220> FEATURE:
<223> OTHER INFORMATION: cleavable linker sequence

<400> SEQUENCE: 7

Gly Phe Leu Gly
1

<210> SEQ ID NO 8
<211> LENGTH: 5
<212> TYPE: PRT
<213> ORGANISM: Artificial
<220> FEATURE:
<223> OTHER INFORMATION: cleavable linker sequence

<400> SEQUENCE: 8

Gly Gly Gly Arg Arg
1               5

<210> SEQ ID NO 9
<211> LENGTH: 4
<212> TYPE: PRT
<213> ORGANISM: Artificial
<220> FEATURE:
<223> OTHER INFORMATION: cleavable linker sequence

<400> SEQUENCE: 9

Ala Phe Lys Lys
1
```

BISPHOSPHONATE-PRODRUGS

CROSS REFERENCE TO RELATED APPLICATIONS

The present application is a 35 U.S.C. 371 National Application of PCT/EP2010/005187, filed Aug. 24, 2010, which claims priority to European Patent Application No. 09 010 871.3, filed Aug. 25, 2009.

The present invention relates to a prodrug, comprising a pharmaceutically and/or diagnostically active compound, and one or more bisphosphonate groups, to a process for producing such a prodrug, and to a pharmaceutical composition comprising said prodrug, to be used for the treatment of bone-related disorders such as bone cancer including metastases.

Healthy bones keep being restructured during their whole lives; about 8% of the entire skeleton is renewed every year. Bone formation and resorption, the so-called remodeling, are in balance and are characteristic of the fully developed bone, bone-forming cells (osteoblasts) and bone-resorbing cells (osteoclasts) taking part in said process. The resorption in bone restructuring starts with binding of the ruffled border of the osteoclasts, an extensive cell membrane, to the bone surface. After surface contact, lysosomal enzymes (e.g. acidic phosphatase or cathepsins) and matrix metalloproteases are secreted, and an ATP-dependent ion pump reduces the pH value in the bone troughs that form the so-called resorption lacunas. At the end of the resorption phase, the osteoclasts are released from the bone surface and osteoblasts or the progenitor cells thereof settle in the lacunae and initiate bone formation.

Bone disorders are characterized by an imbalance between bone formation and bone resorption. For example, when malignant diseases progress, it often happens that micrometastases form, which are often not found in the primary diagnosis. Most commonly, metastases are formed in the liver, in the lungs and in the bones. The symptoms of bone metastasis are serious. In particular, due to the growth of the metastases in the bone marrow, the surrounding bone substance is affected. On the one hand, this is due to pressure damage. On the other hand, the tumor cells secrete substances that change the natural balance between bone formation and bone resorption in the tumor area and thus destroy the bone substance. These processes often result in pain and may finally cause bone fractures that heal very badly. If the spine is affected, there is the additional risk of nerves or the bone marrow itself being crushed due to the collapse of the vertebral bodies. This may lead to symptoms of paralysis and sensation disorders. Moreover, in many cases, the result is a flooding of the blood with calcium, a so-called hypercalcemia.

Bone metastases settle in areas with high blood flow and pronounced remodeling, where growth factors and proteases facilitate the proliferation and invasion of the tumor cells. They are radiographically classified as osteoblastic or osteolytic, which result due to an imbalance between bone formation by osteoblasts and bone resorption by osteoclasts. In addition to the osteoblasts and osteoclasts, bone metastases consist of fibroblasts, macrophages, endothelial cells and the tumor cells of the respective metastasized primary tumor, which together secrete a number of growth factors and proteases, in particular matrix metalloproteases, cathepsins and urokinase, which initiate and promote bone metastasis.

The current treatment of bone metastases is palliative and is based on a combination of chemotherapy, pain therapy and the use of bisphosphonates. The treatment with bisphosphonates reduces the incidence of bone fractures and bone pain and thus improves the quality of life, however without increasing the survival time of the patients. In order to improve the palliative and therapeutic options, new therapeutic approaches are urgently required.

One promising therapeutic approach is bone targeting. In particular, the most striking feature of bone tissue is the mineralized, extracellular matrix with a mineral percentage of about 70% by weight, which primarily consists of apatite $Ca_{10}(PO_4)_6X_2$ wherein X is fluoride (fluorapatite), hydroxy (hydroxyapatite) or chloride (chlorapatite). Moreover, the organic matrix accounts for about 20% by weight and water for about 10% by weight.

In the past, bisphosphonates, tetracyclines, polymalonates and polyaspartates, as well as sialic acid were proposed as osteotropic ligands for bone targeting, wherein the substance class of the bisphosphonates has been best examined.

Bisphosphonates are derivatives of pyrophosphate, in which the central and hydrolytically unstable P—O—P bond is replaced by a stable P—C—P bond.

Bisphosphonates lead to an inactivation of osteoclasts, but other mechanisms of action are postulated as well, e.g. the inhibition of the farnesyl-pyrophosphate synthase or of the matrix metalloproteases. The affinity between the bisphosphonates and the bone apatite is very high.

Also bisphosphonate derivatives with anti-tumor agents such as bisphosphonate complexes of cisplatin analogues and bisphosphonate derivatives of methotrexate have been developed. However, for bisphosphonate complexes of cisplatin analogues significantly higher dosages compared to cisplatin are required. Moreover, the methotrexate bisphosphonate derivative shows a pronounced systemic toxicity.

WO-A-2007/092338 discloses compositions comprising a bisphosphonate and an antifolate. Moreover, WO-A-2008/077241 discloses phosphonated glycopeptides and lipoglycopeptide antibiotics and their use in the treatment of bone and joint infections. WO-A-02/083150 and U.S. Pat. No. 6,214,812 describe bisphosphonate conjugates. However, all of these documents fail to address a prodrug system which is capable of releasing a pharmaceutically active compound selectively at the desired site of action, namely in/on the bone.

Thus, the technical problem underlying the present invention is to provide a target-directed prodrug for the treatment of bone-related disorders such as bone cancer including bone metastases, which should exhibit a more efficient release of a pharmaceutically and/or diagnostically active compound in the bone, and which should exhibit a reduced systemic toxicity as compared to the free pharmaceutically and/or diagnostically active compound, thus leading to less side effects.

According to the present invention, the above technical problem is solved by providing a prodrug which comprises (a) a pharmaceutically and/or diagnostically active compound; (b) a cleavable linker which is bound to the pharmaceutically and/or diagnostically active compound; (c) a spacer group which is bound to the cleavable linker; and (d) one or more bisphosphonate groups which are bound to the spacer group.

In particular, the structure of the prodrug according to the present invention can also be represented by the following structure, wherein a pharmaceutically and/or diagnostically active compound (a) is bound to a cleavable linker (b), which is bound to a spacer group (c), which is bound to one or more bisphosphonate groups (d):

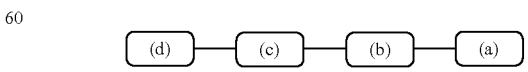

The prodrug according to the present invention is particularly suitable for the treatment of bone-related disorders such as bone cancer including metastases. The prodrug according to the present invention is designed to release the pharmaceutically and/or diagnostically active compound in bone metastases exploiting the acidic environment or the expression of specific enzymes in bone metastases. In particular, bone metastases are characterized by a decreased pH value and by overexpression of specific proteases. The most important proteases overexpressed in bone metastasis are the matrix metalloproteases, the ADMAPs (disintegrin and metalloproteinases), cathepsin B and K and uPA (urokinase-plasminogen activator) as well as tPA (tissue-plasminogen activator) (J. K. Woodward, I. Holen, R. E. Coleman, D. J. Buttle, *Bone* 2007, 41, 912).

Moreover, in order to disintegrate the apatite matrix during bone remodeling and bone metastasis, the pH value must be decreased with respect to the physiological pH value. The pH value in the resorption lacunas is in the acidic range. The pH gradient is ensured by provision of $H^+$ ions by carbonic anhydrase type II, which are transported out of the osteoclasts via the ruffled border by means of an ATP ion pump. By acidification of the extracellular milieu, lysosomally secreted proteases, such as cathepsin B and K, have an ideal milieu for their proteolytic activity. In addition to an overexpression of matrix metalloproteases and ADMAPs (disintegrin and metalloproteinases) in bone metastases, the expression of the urokinase-plasminogen activator (uPA) correlates with the formation of bone metastases.

The pharmaceutically and/or diagnostically active compound (a) is preferably selected from the group consisting of a cytostatic agent, a cytotoxic agent, a cytokine, an immunosuppressant, an antirheumatic, an antiphlogistic, an antibiotic, an analgesic, a virostatic, and an antimycotic agent, a transcription factor inhibitor, a cell cycle modulator, a MDR modulator, a vascular disrupting agent, a proteasome or protease inhibitor, a protein kinase inhibitor, an apoptosis modulator, an enzyme inhibitor, an angiogenesis inhibitor, a hormone or hormone derivative, a radioactive substance, a light emitting substance, and a light absorbing substance.

In view of an application of the prodrug as an anti-tumor agent, it is preferred that the pharmaceutically and/or diagnostically active compound is a cytostatic agent selected from the group consisting of N-nitrosoureas, the anthracyclines doxorubicin, 2-pyrollinoanthracycline, morpholinoanthracycline, diacetatoxyalkylanthracycline, daunorubicin, epirubicin, idarubicin, mitoxantrone and ametantrone, and any derivatives thereof; the alkylating agents chlorambucil, bendamustine, melphalan, and oxazaphosphorines, and any derivatives thereof; the antimetabolites 5-fluorouracil, 2'-deoxy-5-fluorouridine, cytarabine, cladribine, fludarabine, pentostatine, gemcitabine, 6-thioguanine and 6-mercaptopurine, and any derivatives thereof; the folic acid antagonists methotrexate, raltitrexed, pemetrexed and plevitrexed, the taxanes paclitaxel and docetaxel, and any derivatives thereof; the camptothecins topotecan, irinotecan, SN-38, 10-hydroxycamptothecin, GG211, lurtotecan, 9-aminocamptothecin and camptothecin, and any derivatives thereof; the Vinca alkaloids vinblastine, vincristine, vindesine and vinorelbine, and any derivatives thereof; calicheamicins and any derivatives thereof; maytansinoids and any derivatives thereof; auristatins and any derivatives thereof; epothilones and any derivatives thereof; duocarmycins and any derivatives thereof; bleomycin, dactinomycin, plicamycin, mitomycin C and cis-configured platinum(II) complexes.

In order to be bound to the cleavable linker (b), the pharmaceutically and/or diagnostically active compound (a) may be derivatized. Accordingly, in order to contain a suitable moiety for chemical derivatization, the pharmaceutically and/or diagnostically active compound to be used to prepare the prodrug of the present invention may contain at least one functional group selected from —COOH, —OH, —NH$_2$, —NH—NH$_2$, —CO—NH—NH$_2$, —SO$_3$H, —SH or a carbonyl group.

According to the present invention, the cleavable linker (b) comprises a group which can be cleaved. Said cleavage preferably takes place at the desired site of action, e.g. in bones, in particular in bone metastases. Since bone metastases are characterized by a decreased pH value and by overexpression of specific enzymes, it is preferred that the cleavable linker comprises a group which can be cleaved enzymatically and/or pH-dependently. For example, the cleavable linker of the prodrug of the present invention may contain at least one peptide bond which is preferably located within a cleavable peptide sequence of a protease. A peptide bond can therefore be implemented by the insertion of a respective peptide sequence into the cleavable linker. Suitable enzymes are, for example, proteases and peptidases, e.g. matrix metalloproteases (MMP), cysteine proteases, serine proteases and plasmin activators, which are formed or activated in intensified manner in diseases such as rheumatoid arthritis or cancer, leading to excessive tissue degradation, inflammations and metastasis. Preferred examples of enzymes are the metalloproteases, the ADMAPs (disintegrin and metalloproteinases), cathepsin B and K and uPA (urokinase-plasminogen activator) as well as tPA (tissue-plasminogen activator), since these enzymes are generally overexpressed in bone metastases.

In a preferred embodiment of the present invention, the cleavable linker comprises an enzymatically cleavable peptide sequence selected from the group consisting of -Arg-, -Arg-Arg-, -Phe-Arg-, -Phe-Cit-, -Ile-Pro-Lys-, -Lys-, -Lys-Lys-, -Arg-Lys-, -Leu-Arg-, -Phe-Arg-, -Val-Arg-, -Ala-Leu-Ala-Leu- [SEQ ID NO:1], -Phe-Lys-, -Phe-Lys-Ala-, -Val-Cit-, -Val-Ala-, -Val-Arg-, -Ala-Phe-Lys-, -D-Ala-Phe-Lys-, -Ser-Ser-Tyr-Tyr-Ser-Arg- [SEQ ID NO:2], -Phe-Pro-Lys-Phe-Phe-Ser-Arg-Gln- [SEQ ID NO:3], -Lys-Pro-Ile-Glu-Phe-Nph-Arg-Leu- [SEQ ID NO:4], -Gly-Pro-Leu-Gly-Ile-Ala-Gly-Gln- [SEQ ID NO:5], -Gly-Pro-Gln-Gly-Ile-Trp-Gly-Gln- [SEQ ID NO:6], -Gly-Phe-Leu-Gly- [SEQ ID NO:7], -Gly-Gly-, -Gly-Gly-Gly- and -Gly-Gly-Gly-Arg-Arg- [SEQ ID NO:8].

In another preferred embodiment of the present invention, the cleavable linker comprises an acid-sensitive group which can be cleaved upon a decrease in the pH-value. Preferably, this acid-sensitive group contains at least one acid-sensitive bond. It is particularly preferable that the acid-sensitive group is selected from ester, acetal, ketal, imine, hydrazone, acylhydrazone and sulfonylhydrazone bonds or bonds containing a trityl group. Because bone metastases are generally characterized by a decreased pH value, such acid-sensitive groups can be cleaved at the desired site, namely the metastasis.

In order to release the pharmaceutically and/or diagnostically active compound, the cleavable group is cleaved at the desired site of action, thus setting free the pharmaceutically and/or diagnostically active compound. The cleavable linker (b) may further contain one or more self-immolative groups which produce, after peptide cleavage or cleavage of an acid-sensitive bond, a labile self-immolative spacer drug derivative that in turn hydrolyzes in a spontaneous reaction and releases the pharmaceutically and/or diagnostically active compound. Preferably, the cleavable linker comprises a self-immolative group which is selected from one of the following groups:

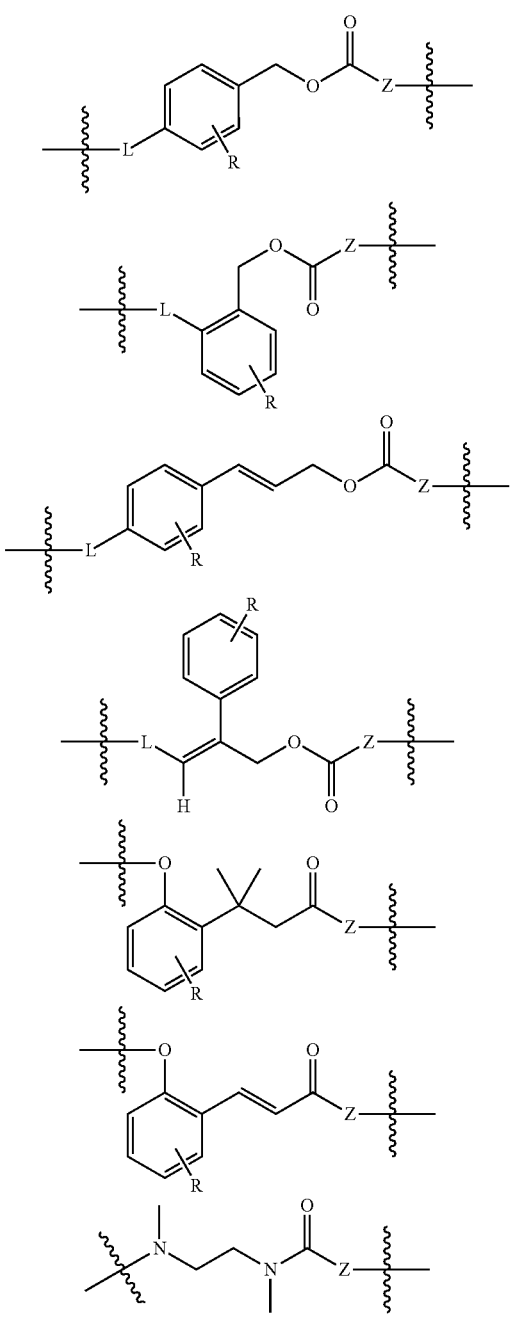

wherein the pharmaceutically and/or diagnostically active compound (a) is bound to the Z-terminus of the self-immolative group, wherein Z and L are independently selected from O, S and NH, and R represents one or more substituents at the phenyl ring which are independently selected from the group consisting of F, Cl, Br, I, $NO_2$, CN, OH, a $C_{1-8}$ alkyl group and a $C_{1-6}$ aryl group.

Moreover, the prodrug according to the present invention further comprises a spacer group (c) which is bound to the cleavable linker (b). This group may have the function as a mere spacer, but also to enhance water-solubility, bio-compatibility and/or molecular mass of the prodrug. Moreover, the spacer group (c) can also be present only for synthetic reasons, namely to enable a connection of the cleavable linker (b) to the one or more bisphosphonate groups (d) by a convenient synthetic route. Accordingly, the spacer group (c) is not restricted and may comprise any groups which enable a convenient connection of the cleavable linker (b) to the one or more bisphosphonate groups (d).

The spacer group (c) may be bound to the one or more bisphosphonate groups (d) for example through an amide bond, an ester bond, an ether bond, a thioether bond, a disulfide bond, or a carbon-carbon single bond, a carbon-carbon double bond or a carbon-carbon triple bond.

For example, the spacer group (c) may comprise a unit obtained from the group consisting of a maleinimide group, a halogenacetamide group, a halogenacetate group, a pyridylthio group, a vinyl carbonyl group, an aziridin group, a disulfide group, and a substituted or unsubstituted acetylene group. In particular, after addition of a suitable reagent, the above groups may have the following exemplarily shown structures, wherein Z may be O, S or NH:

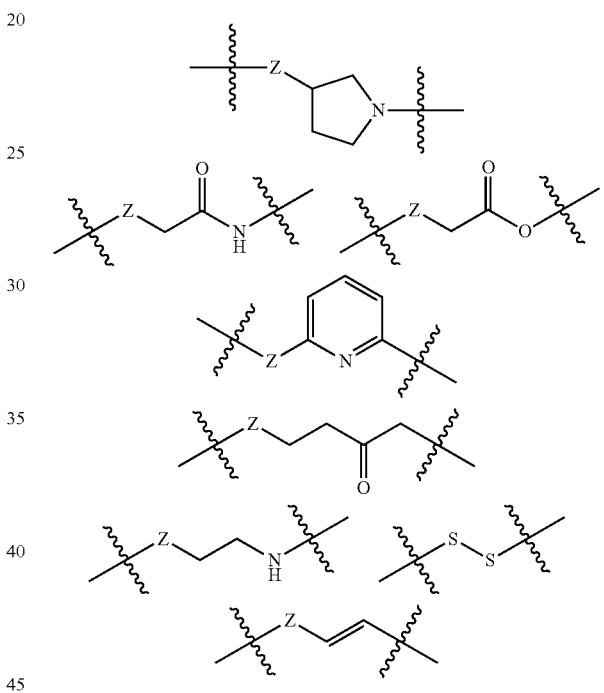

In a further preferred embodiment of the present invention, the spacer group (c) may also comprise an aliphatic chain —$(CH_2)_n$— with n being an integer of from 1 to 12, an oligoethylene glycol —$(O—CH_2—CH_2)_n$— with n being an integer of from 1 to 12, a synthetic poly(ethylene glycol), or a phenyl ring, optionally substituted with one or more substituents selected from the group consisting of F, Cl, Br, I, $NO_2$, $SO_3H$, CN, OH, COOH, a $C_{1-8}$ alkyl group and a $C_{1-6}$ aryl group, or combinations thereof. It is particularly preferred that the spacer group contains a synthetic polymer selected from the group consisting of poly(ethylene glycol) (PEG), monomethoxy PEG (mPEG), polyglycerol (PG), poly (ethylene imine) (PEI) and N-(2-hydroxypropyl)methacrylamide (HPMA) copolymers, and combinations thereof. It is particularly preferable that the spacer group comprises PEG having a mass e.g. ranging from 1,000 to 50,000 Da. It is more preferred that the PEG has a mass in the range of from 2,000 to 20,000 Da. Examples of such spacer groups can be derived from commercially available protected mercapto derivatives of PEG of the following structure SuOOC—$CH_2$—$CH_2$-PEG-$CH_2$—$CH_2$—S-Trt. This group can be converted into a unit for the spacer group having the structure —OOC—CH$_2$—CH$_2$-PEG-CH$_2$—CH$_2$—S—.

The above linker groups may be advantageous from the viewpoint of an efficient synthesis of the prodrug. Moreover, the synthetic polymer may be advantageous from the viewpoint of enhancing water-solubility, bio-compatibility, molecular mass and biodistribution of the prodrug.

According to the present invention, the prodrug comprises one or more bisphosphonate groups (d) which are bound to the spacer group. In a preferred embodiment of the present invention, the prodrug contains 1 to 12 bisphosphonate groups. It is particularly preferred that the prodrug contains one, two or three bisphosphonate groups. The bisphosphonate groups can be selected from any suitable bisphosphonate groups. In a preferred embodiment of the present invention, the one or more bisphosphonate groups are independently selected from the group consisting of etidronate, clodronate, tiludronate, pamidronate, 1-amino-1,1-diphosphonate methane (aminoBP), risedronate, ibandronate, 1-hydroxy ethylidene-1,1-diphosphonic acid (HEDP), alendronate and zoledronate. The above bisphosphonates may be chemically modified in such a manner that they can be attached to the spacer group. In a particularly preferred embodiment of the present invention, the bisphosphonate group is pamidronate.

In another preferred embodiment, the one of more bisphosphonate groups (d) have independently one of the following structures (IIa) to (Va) or (IIb) to (Vb):

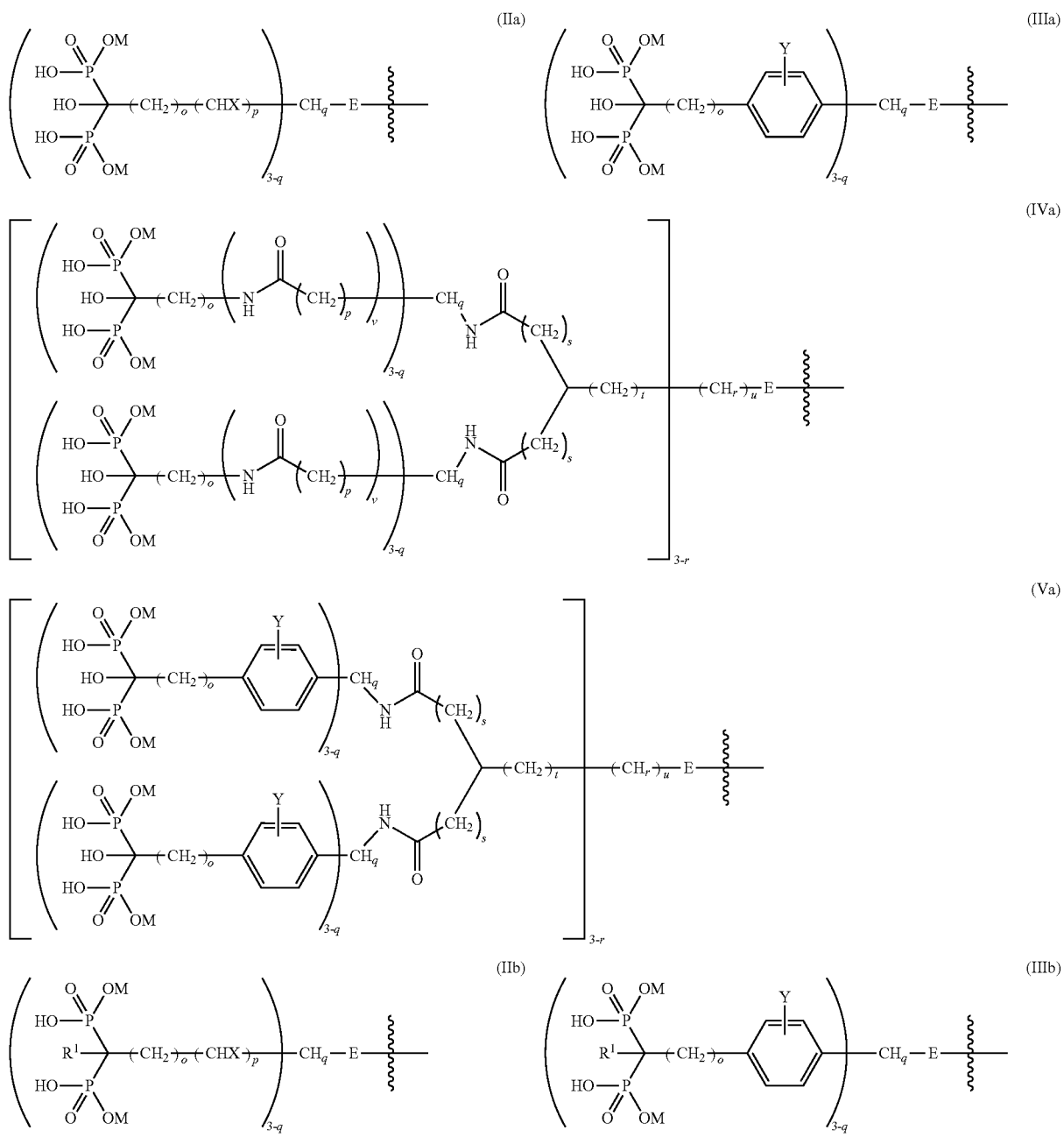

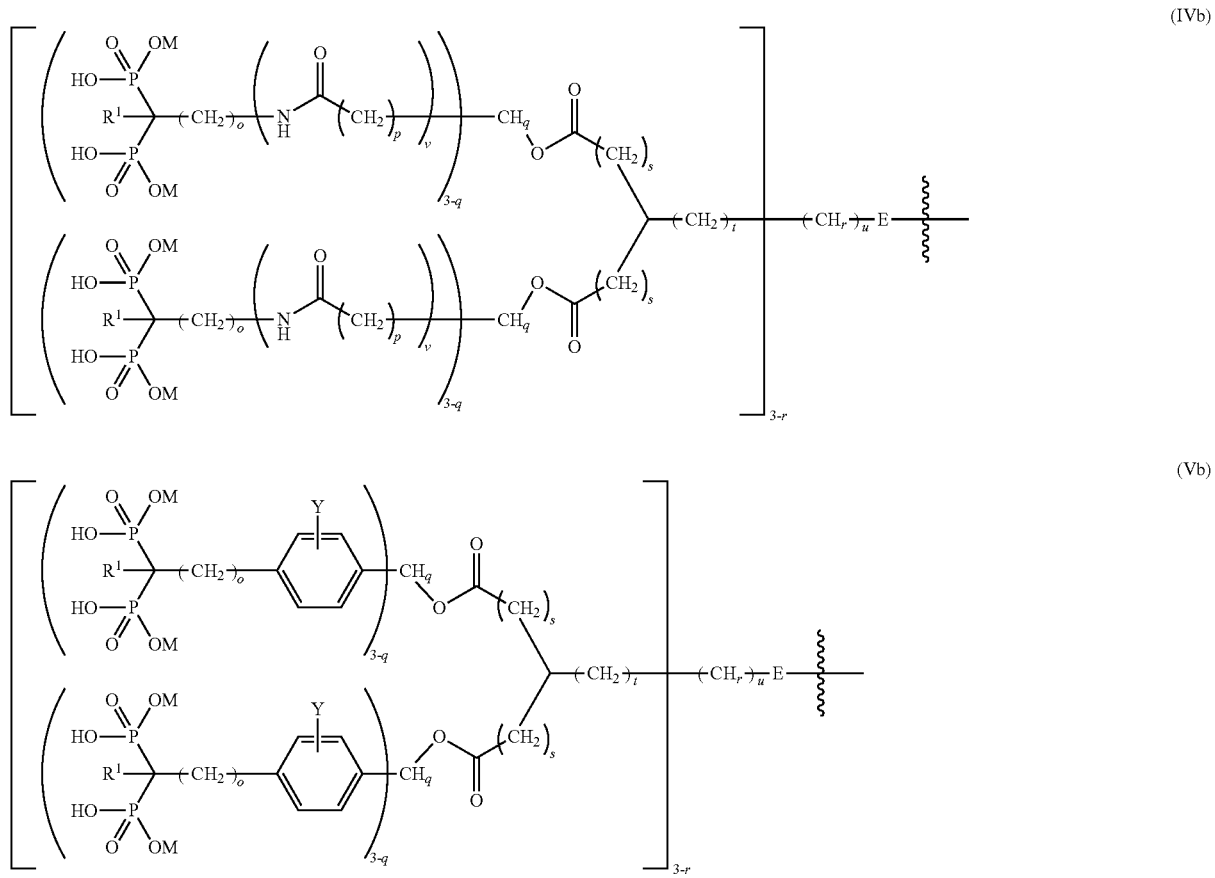

wherein
o is an integer independently selected from 0 to 12,
p is an integer independently selected from 0 to 2,
q is an integer independently selected from 0 to 2,
r is an integer independently selected from 1 or 2,
s is an integer independently selected from 0 to 12,
t is an integer independently selected from 0 to 2,
u is an integer independently selected from 0 or 1,
v is an integer independently selected from 0 to 2,
each of X and Y are independently selected from the group consisting of F, Cl, Br, I, $NO_2$, $SO_3H$, CN, OH, COOH, $COOCH_3$, —CHO, —$CHOCH_3$, an $C_{1-8}$ alkyl group and an $C_{1-6}$ aryl group, $R^1$ may be the same or different and is independently selected from the group consisting of F, Cl, Br, I, $NO_2$, CN, $COOCH_3$, —CHO, —$CHOCH_3$, an $C_{1-8}$ alkyl group and an $C_{1-8}$ aryl group, E represents O, NH, a carbon-carbon single bond, a carbon-carbon double bond or a carbon-carbon triple bond, and M is independently selected from hydrogen, sodium, potassium, calcium and magnesium.

According to the present invention, the different components (a), (b), (c) and (d) can be arbitrarily combined without any restrictions, to give the prodrug of the present invention.

In a preferred embodiment of the present invention, the prodrug has the following general formula (I):

(I)

wherein the unit (d) represents the one or more bisphosphonate groups having one of the above structures (II) to (V), wherein the unit (c) represents the spacer group, wherein the unit (b) represents the cleavable linker, and wherein the unit (a) represents the pharmaceutically and/or diagnostically active compound.

In the above prodrug of general formula (I), it is preferred that the unit (d) is selected from one of the following structures (VIa) to (VIIIa) or (VIb) to (VIIIb):

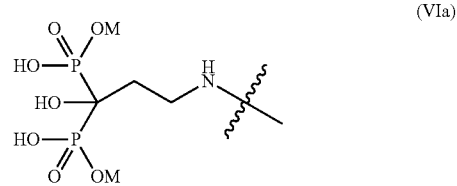

(VIa)

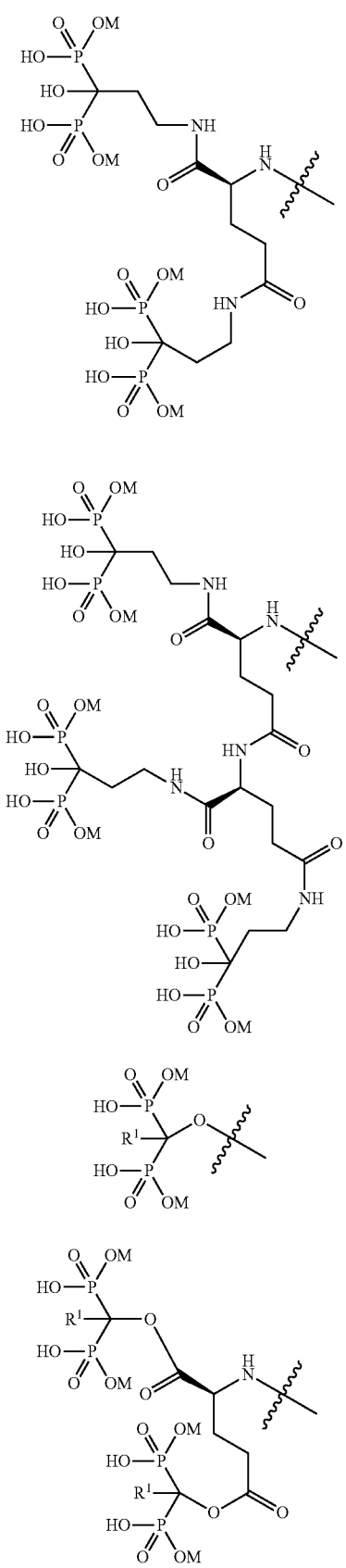

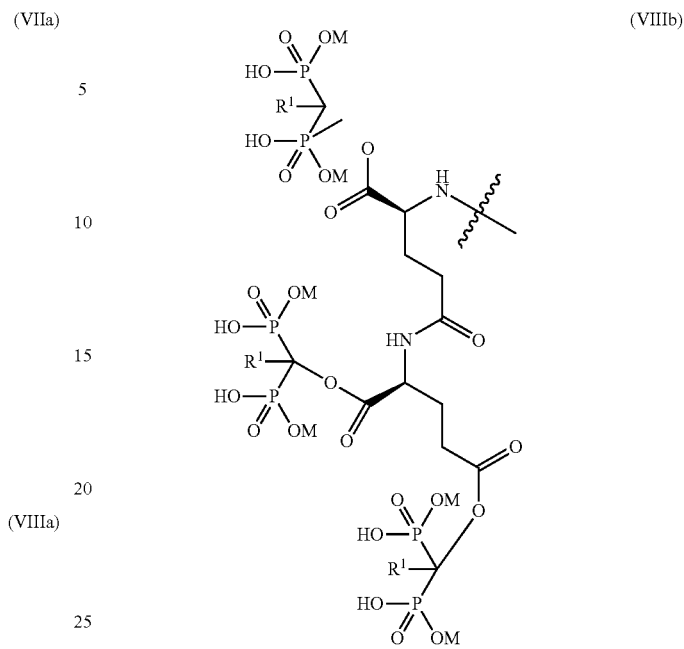

wherein $R^1$ may be the same or different and is independently selected from the group consisting of F, Cl, Br, I, $NO_2$, CN, $COOCH_3$, —CHO, —$CHOCH_3$, an $C_{1-8}$ alkyl group and an $C_{1-6}$ aryl group, and M is independently selected from hydrogen, sodium, potassium, calcium and magnesium.

In the above prodrug of general formula (I), it is also preferred that the unit (c) is selected from one of the following structures (IX) to (XII):

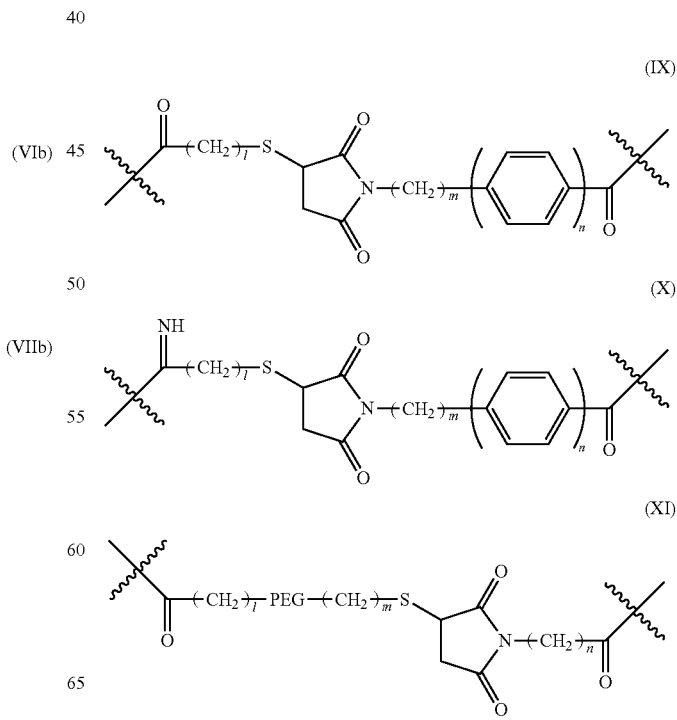

-continued

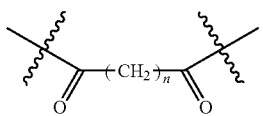
(XII)

In the above structures (IX) to (XII), l, m and n are independently selected from an integer of from 0 to 12. In above structures (IX) and (X), m is preferably 0, when n is an integer of from 1 to 12, and n is preferably 0, when m is an integer of from 1 to 12. In above structures (IX) and (X), it is particularly preferred that l is 3, m is 5 and n is 0. In above structure (XI), PEG represents poly(ethylene glycol), l and m are preferably 2, and n is preferably 5.

In the above prodrug of general formula (I), it is further preferred that the units (a) and (b) taken together are selected from one of the following structures (XIII) to (XVII):

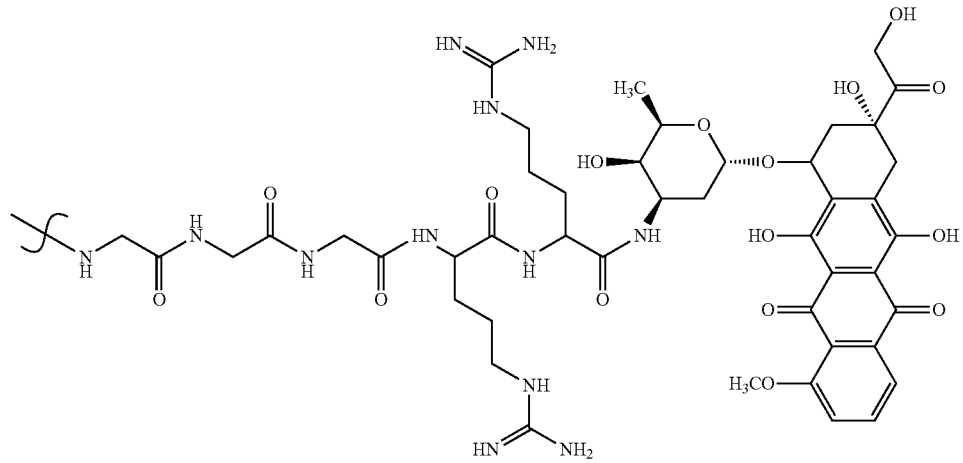
(XIII)

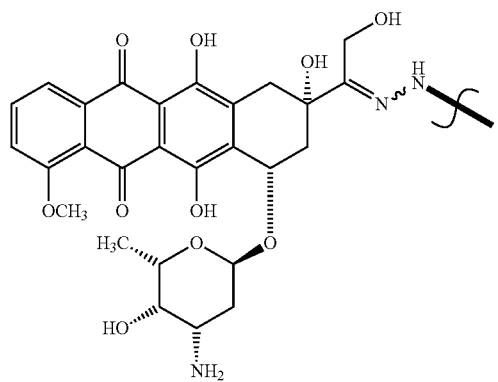
(XIV)

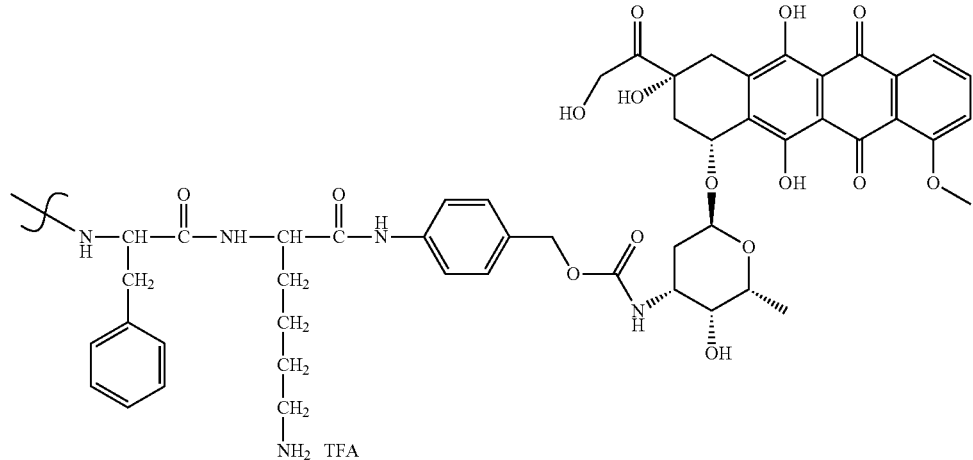
(XV)

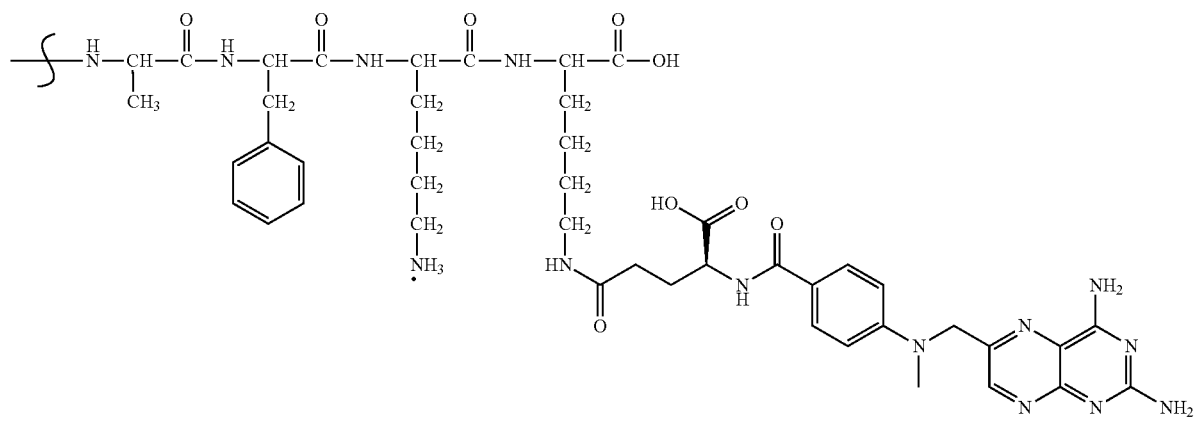

(XVI)

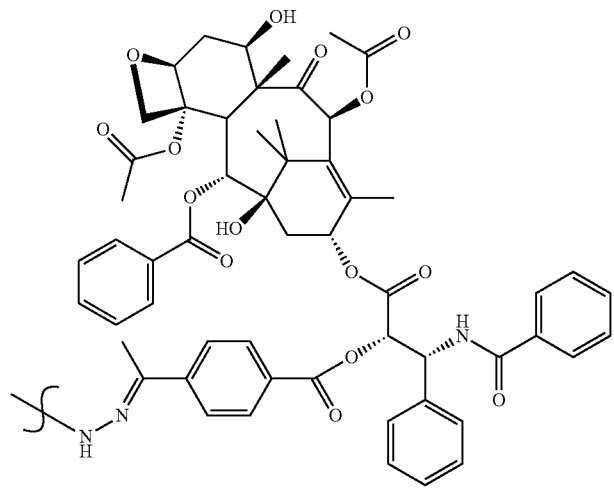

(XVII)

In above unit (XIII), the cleavable linker comprises a Gly-Gly-Gly-Arg-Arg [SEQ ID NO:8] peptide sequence which can be cleaved by urokinase. In above units (XIV) and (XVII), the cleavable linker comprises a hydrazone unit which is acid labile. In above unit (XV), the cleavable linker comprises a Phe-Lys peptide sequence which can be cleaved by cathepsin B.

Another aspect of the present invention relates to a pharmaceutical composition, comprising the prodrug as defined above, and optionally a pharmaceutically acceptable carrier and/or a pharmaceutically acceptable adjuvant and/or a diluent.

The pharmaceutical composition may for example contain solvents and diluents such as sodium chloride solution or a solution containing any pharmaceutically acceptable buffer. Moreover, the pharmaceutical composition of the present invention may be in any form suitable for administration to a patient, for example in an injectable form, as a tablette or a capsule, or as a composition for inhalation.

According to a specific embodiment, the above-defined pharmaceutical composition is used for the treatment of a bone-related disorder, in particular for the treatment of bone cancer including bone metastases.

According to another embodiment of the present invention, the prodrug as defined above may be comprised in a kit, which may further contain one or more adjuvants, such as a buffer or a pharmaceutically acceptable carrier.

The synthesis pathway of the prodrug of the present invention is not restricted. In one example, the prodrug of the present invention can be synthesized using a building block comprising a maleinimide group, the cleavable linker and the pharmaceutically and/or diagnostically active compound. The synthesis of said building block is known from the prior art (cf. for example D. E. Chung, F. Kratz, *Bioorg. Med. Chem. Lett.* 2006, 16, 5157-5163; F. Kratz, *Expert. Opin. Investig. Drugs* 2007, 16, 855-866). Examples for these building block are the following compounds (XVIII) to (XXII):

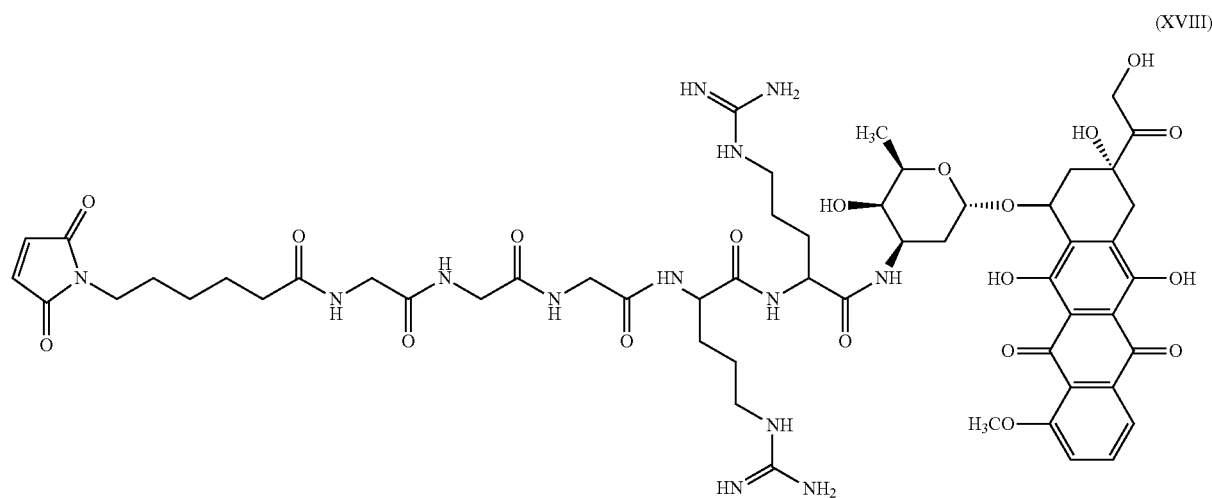
(XVIII)
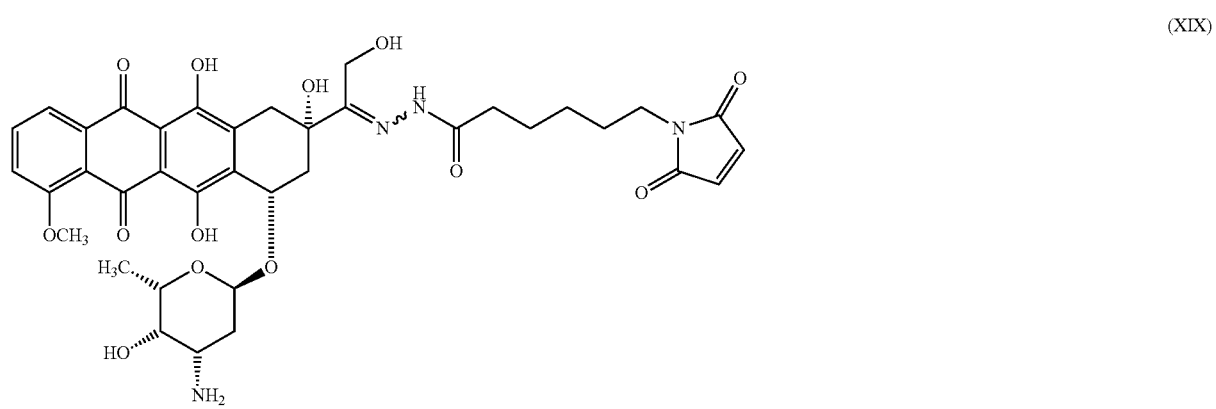
(XIX)
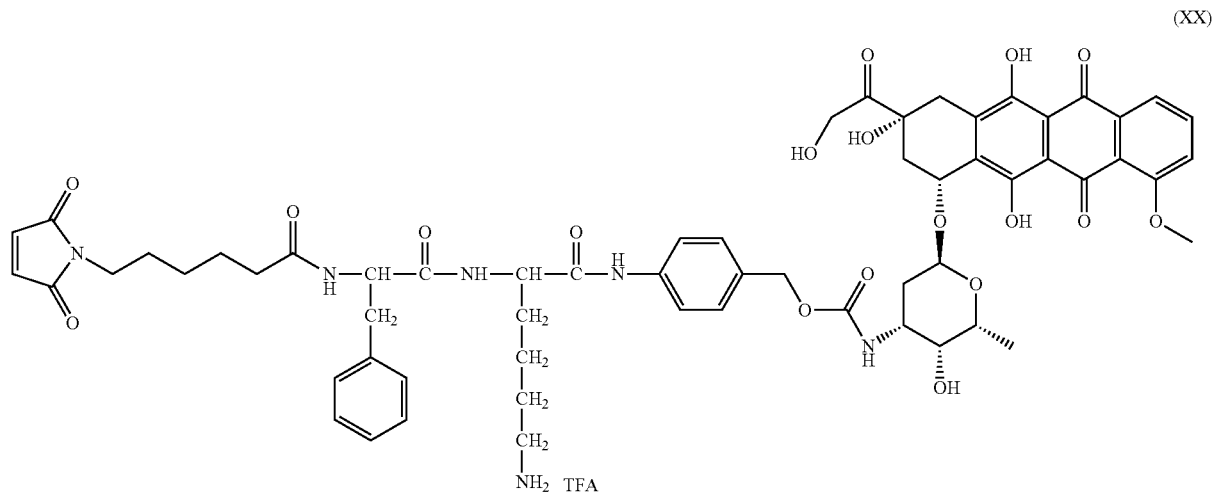
(XX)

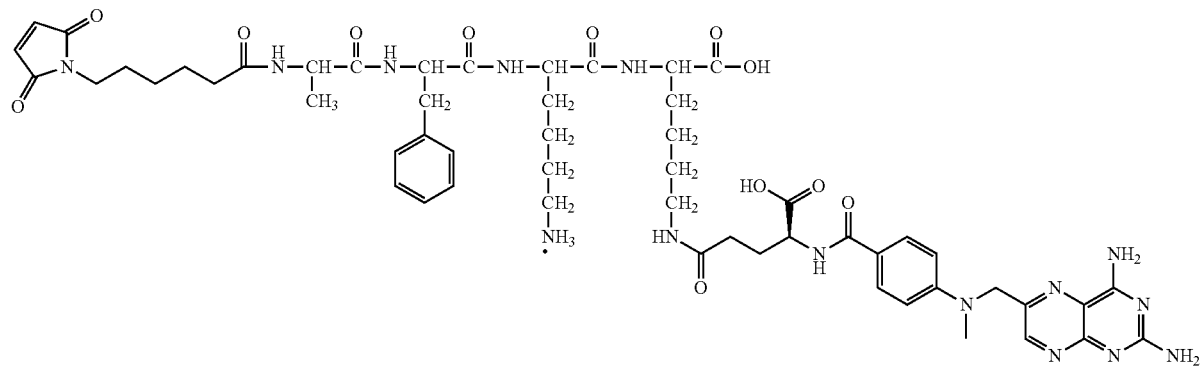

(XXI)

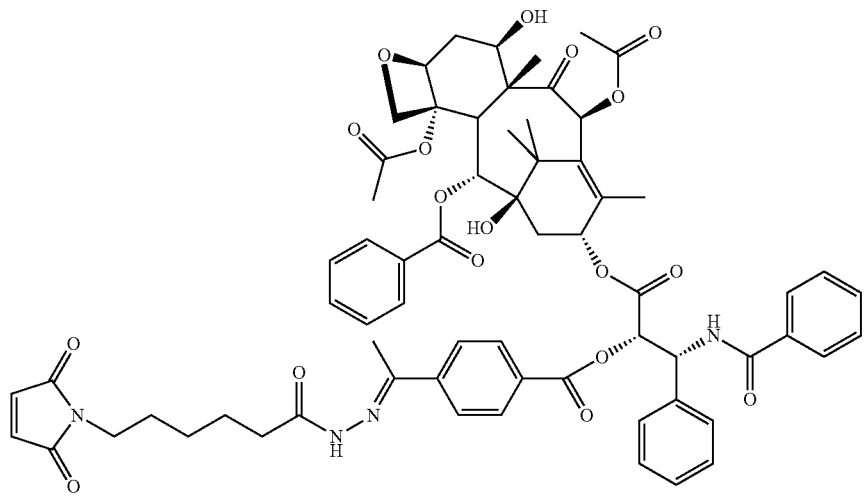

(XXII)

The building block comprising a maleinimide group (such as the compounds represented by above structures (XVIII) to (XXII)) can be reacted with a thiolated derivative of the bisphosphonate(s) to give the prodrug of the present invention. Examples of thiolated derivatives of the bisphosphonate(s) are the following compounds (XXIII), (XXIVa/b), (XXVa/b), (XXVIa/b), and (XXVIIa/b):

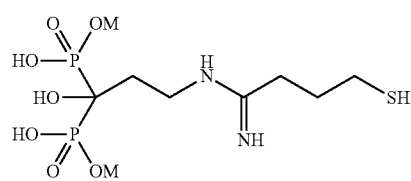

(XXIII)

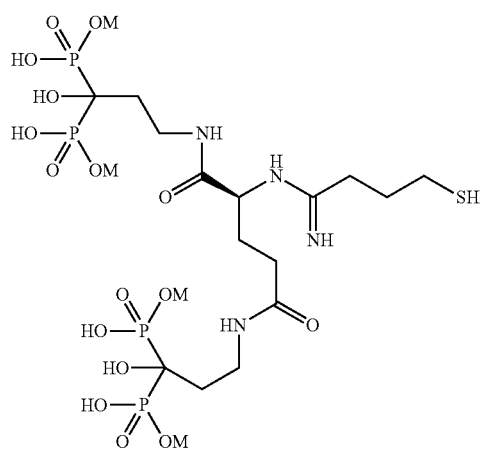

(XXIVa)

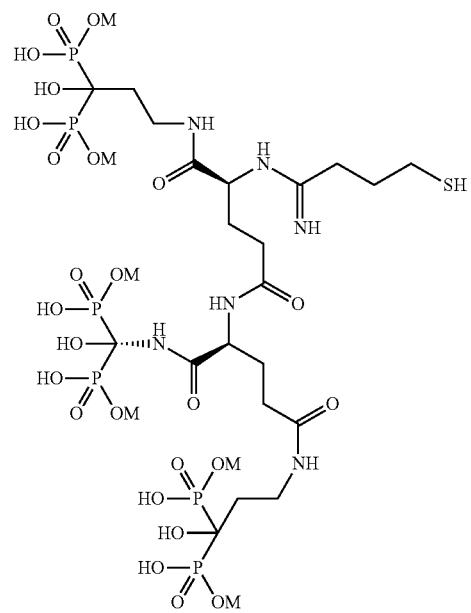
(XXVa)

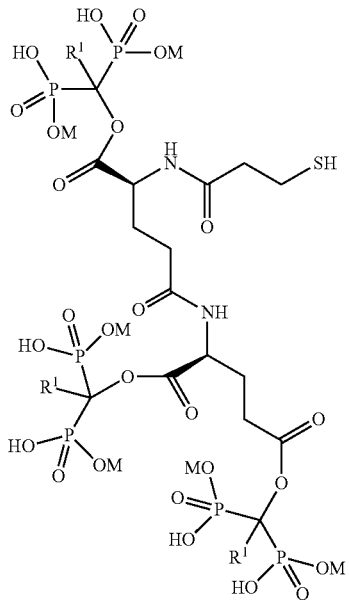
(XXVb)

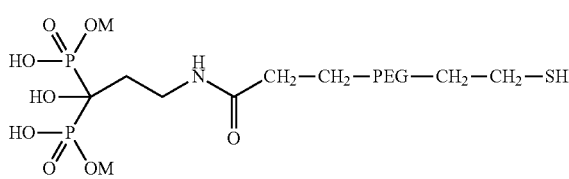
(XXVIa)

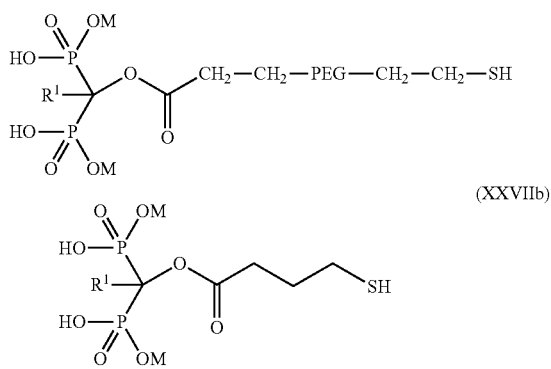
(XXVIb)

(XXVIIa)
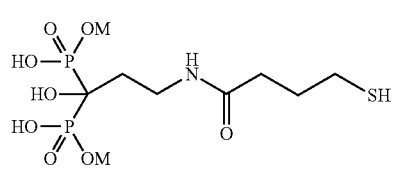

(XXVIIb)

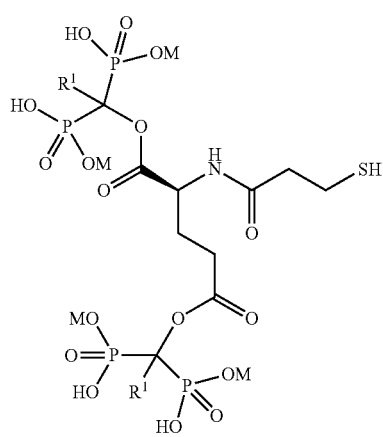
(XXIVb)

The above compounds (XXIII), (XXIVa) and (XXVa) are available by reacting the amine group of the bisphosphonate(s) with an iminothiolane. The residue $R^1$ is as defined above. For the synthesis of above compound (XXVIa), protected mercapto derivatives of PEG having a molecular weight of 2,000, 5,000, 10,000 and 20,000 Da can be used. Such compounds are commercially available. Said PEG derivatives further contain an activated N-hydroxysuccinimide ester group which can be used for the introduction of the bisphosphonate. The general synthetic schemes for producing above compounds (XXIII) to (XXVIIb) are shown in FIGS. 1 to 5 and 7 to 10.

Moreover, it is possible to carry out the reaction of the bisphosphonate(s) with the iminothiolane and the reaction with the maleinimid containing building block in a one step reaction. The purification of compounds of the present invention can be achieved via preparative HPLC.

Alliteratively, it is also possible to synthesize the prodrug according to the present invention without using a building block comprising a maleinimide unit. One example for such an approach is shown in FIG. 6.

The Figures show:
FIG. 1 shows a general scheme of the synthesis of the compound of formula (XXIII).
FIG. 2 shows a general scheme of the synthesis of the compound of formula (XXIVa).

EXAMPLE 1

Synthesis of a bisphosphonate prodrug with a methotrexate prodrug (EMC-D-Ala-Phe-Lys-Lys-(gamma-MTX)-OH [SEQ ID NO:9] (EMC=6-maleimidocaproic acid; MTX=methotexate). EMC-D-Ala-Phe-Lys-Lys-(gamma-MTX)-OH [SEQ ID NO:9] is cleaved between Lys-Lys by Cathepsin B and plasmin and releases (gamma-MTX) as reported in A. Warnecke et al., Arch. Pharm. 2007, 340, 389-395.

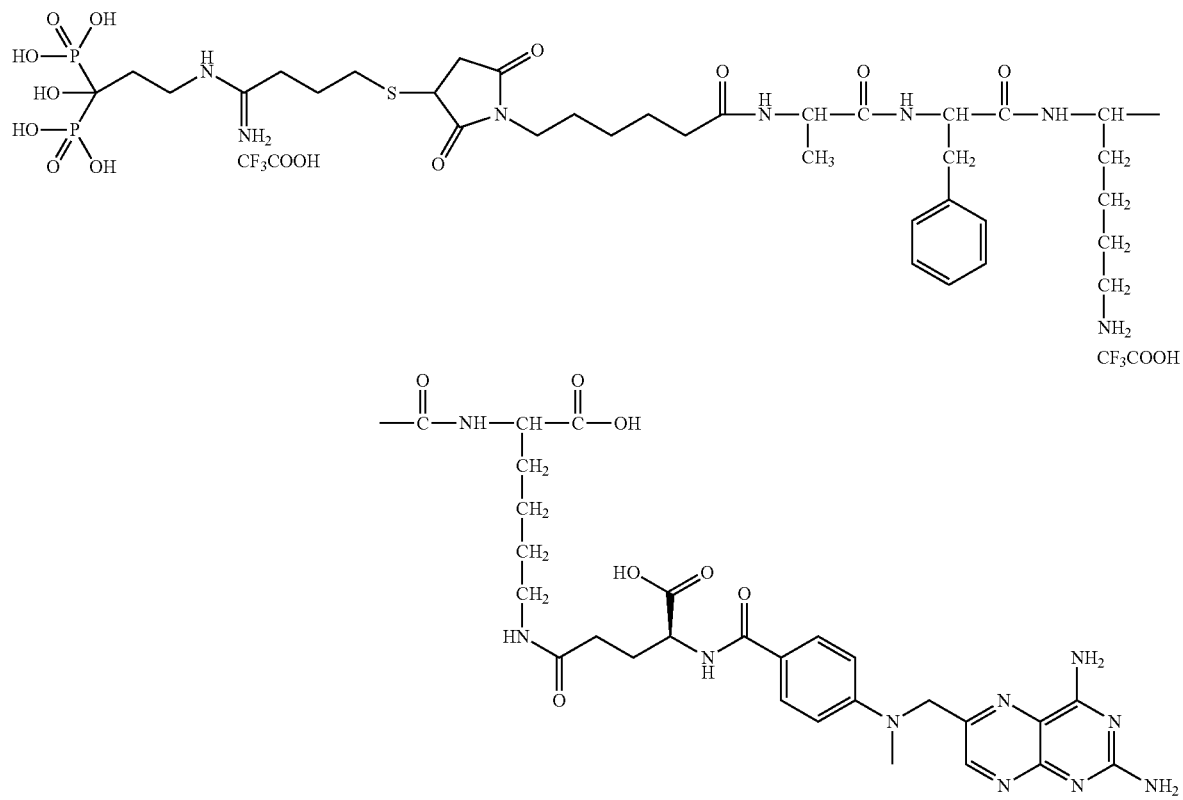

Figure 1:
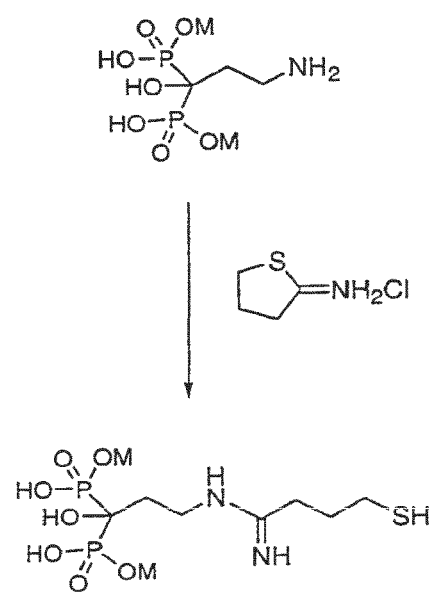
Figure 2:
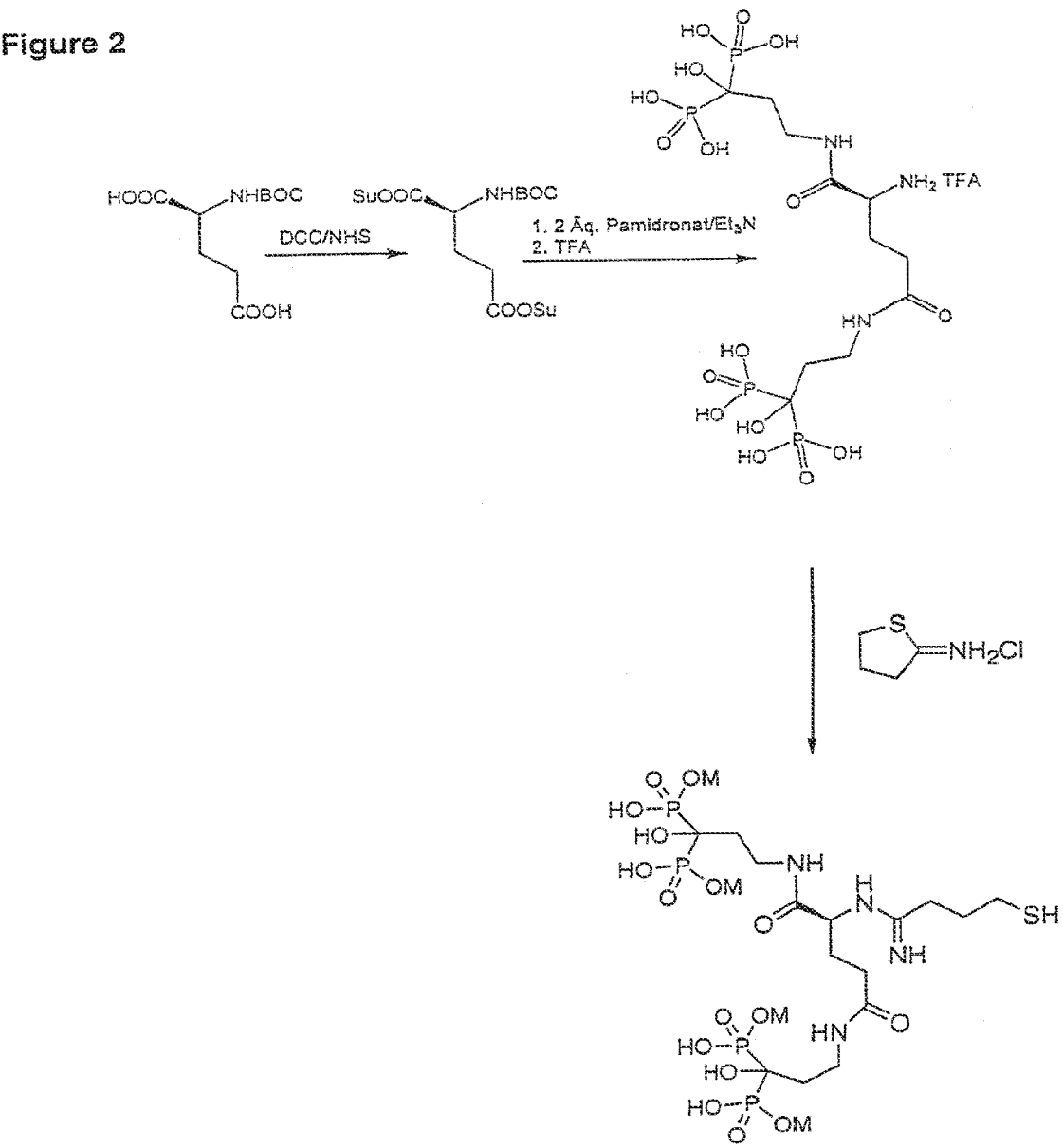
Figure 3:
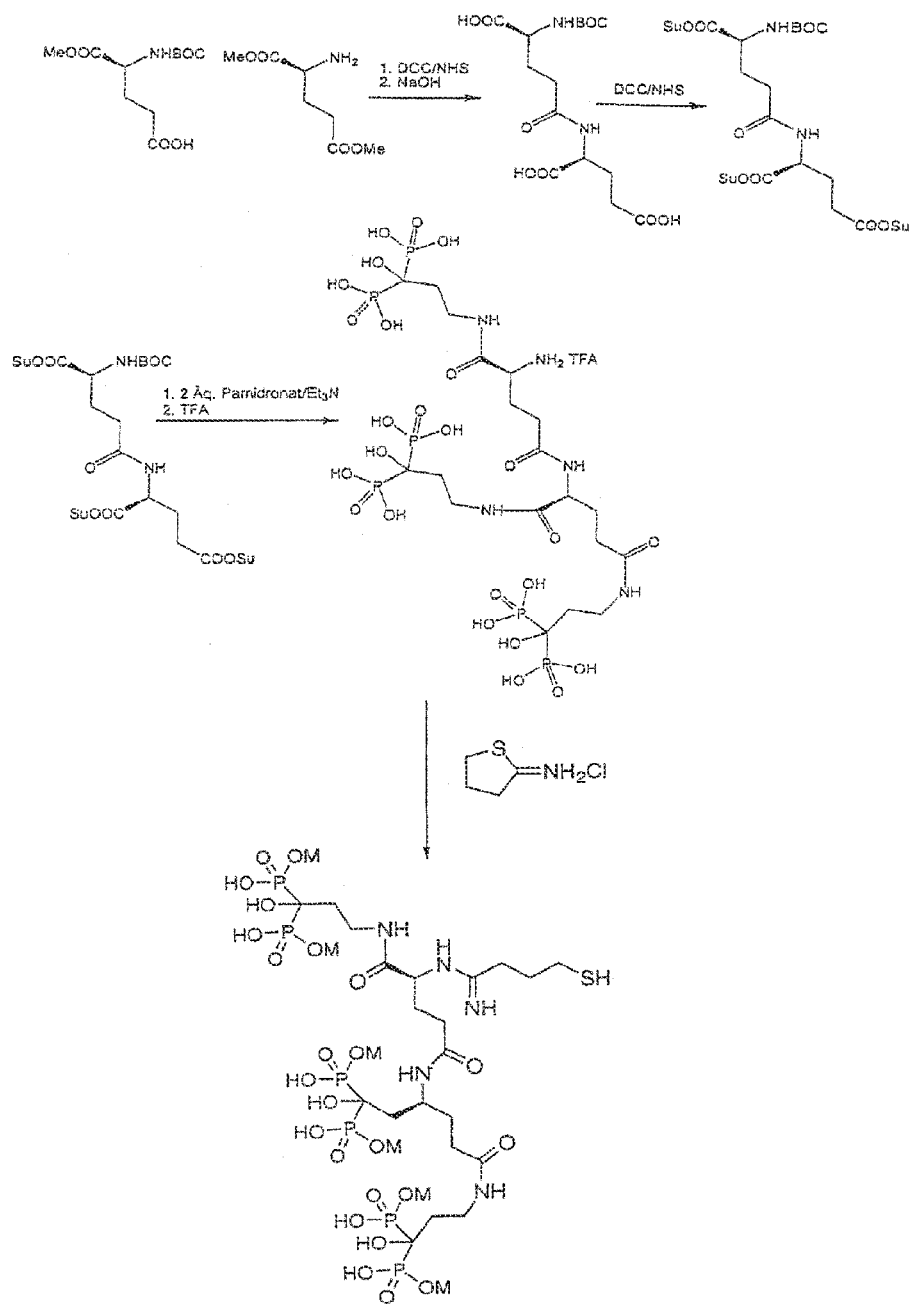
FIG. 3 shows a general scheme of the synthesis of the compound of formula (XXVa).
Figure 4:
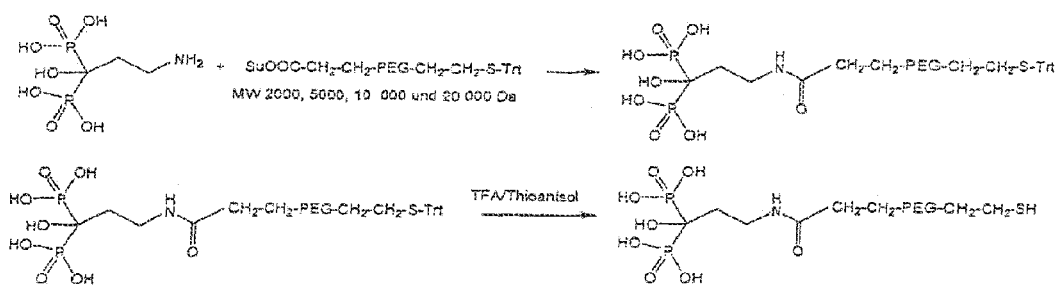
FIG. 4 shows a general scheme of the synthesis of the compound of formula (XXVIa).
Figure 5:
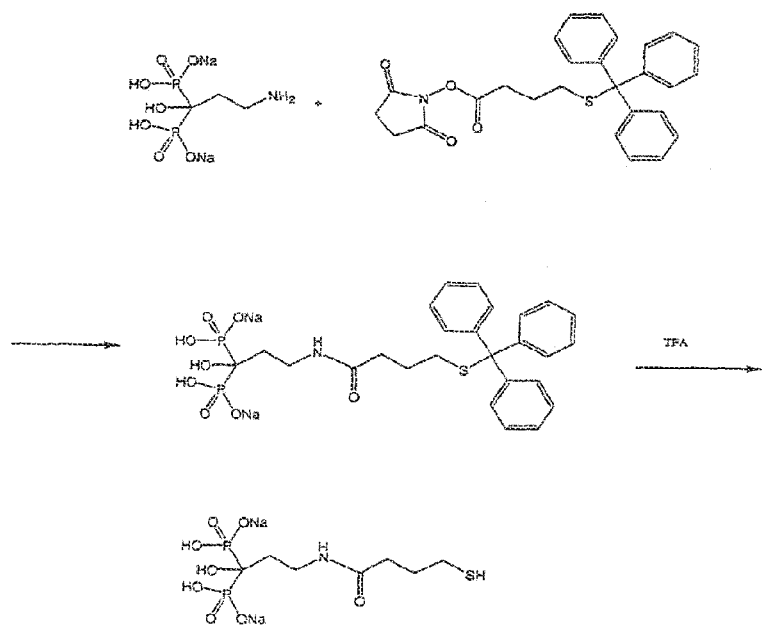
FIG. 5 shows a general scheme of the synthesis of the compound of formula (XXVIIa).
Figure 6:
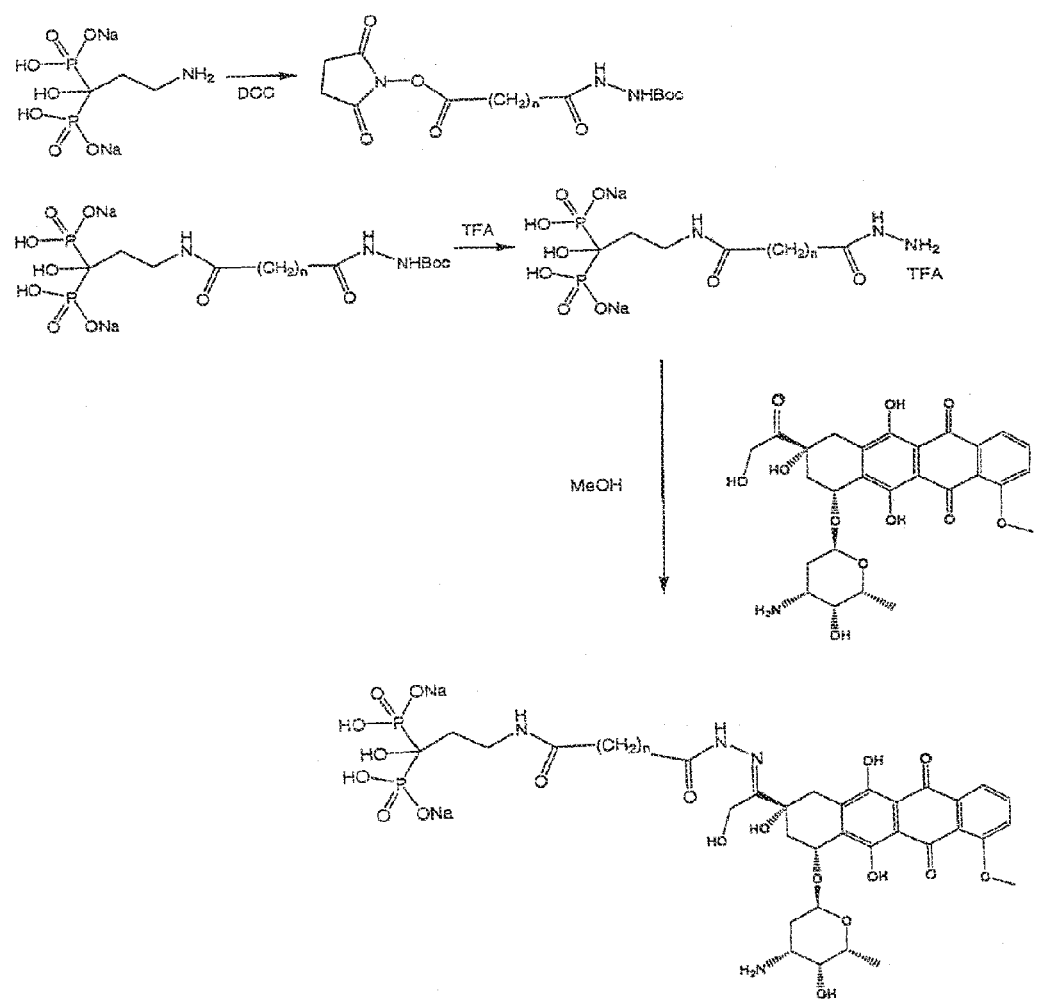
FIG. 6 shows an example for the synthesis for a prodrug according to the present invention which does not make use of a building unit comprising a maleinimide unit.
Figure 7:
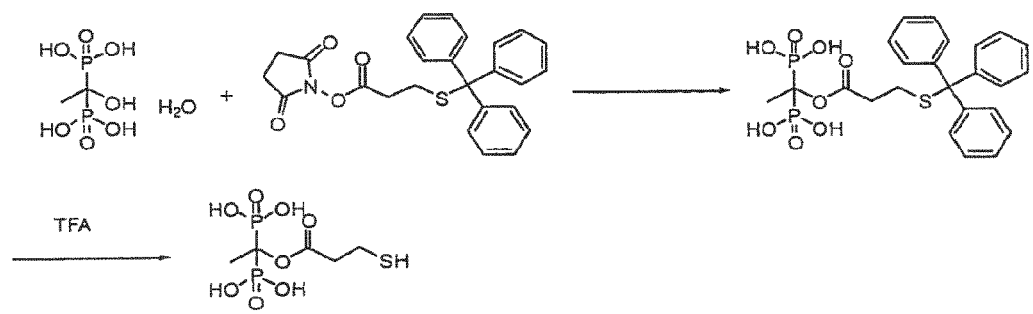
FIG. 7 shows a general scheme of the synthesis of the compound of formula (XXVIIb).
Figure 8:
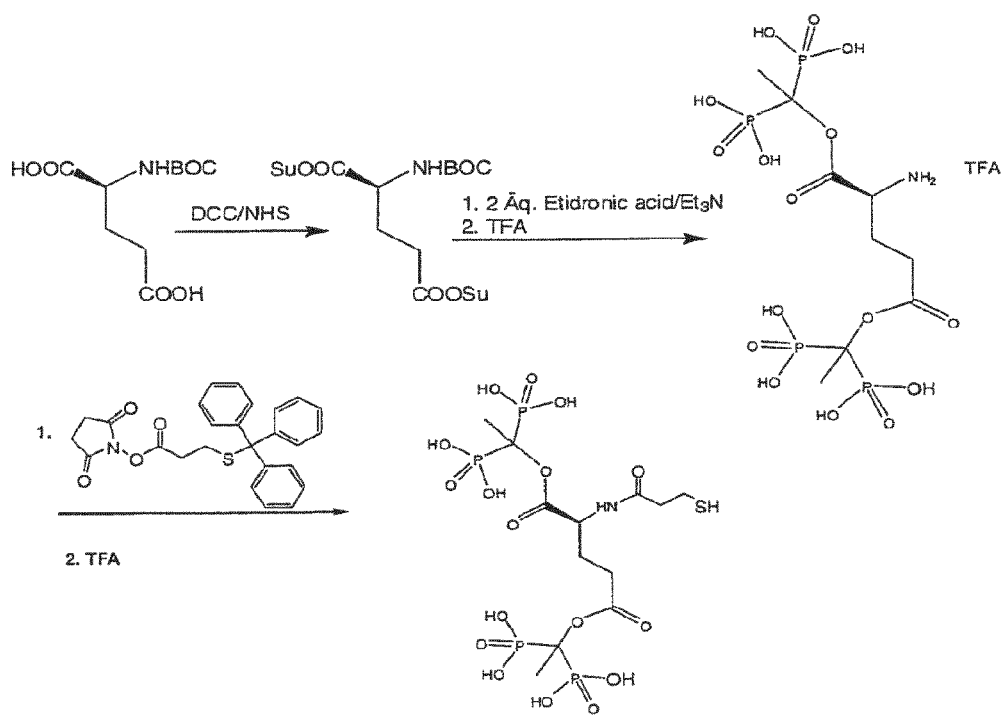

FIG. 8 shows a general scheme of the synthesis of the compound of formula (XXIVb).

Figure 9:
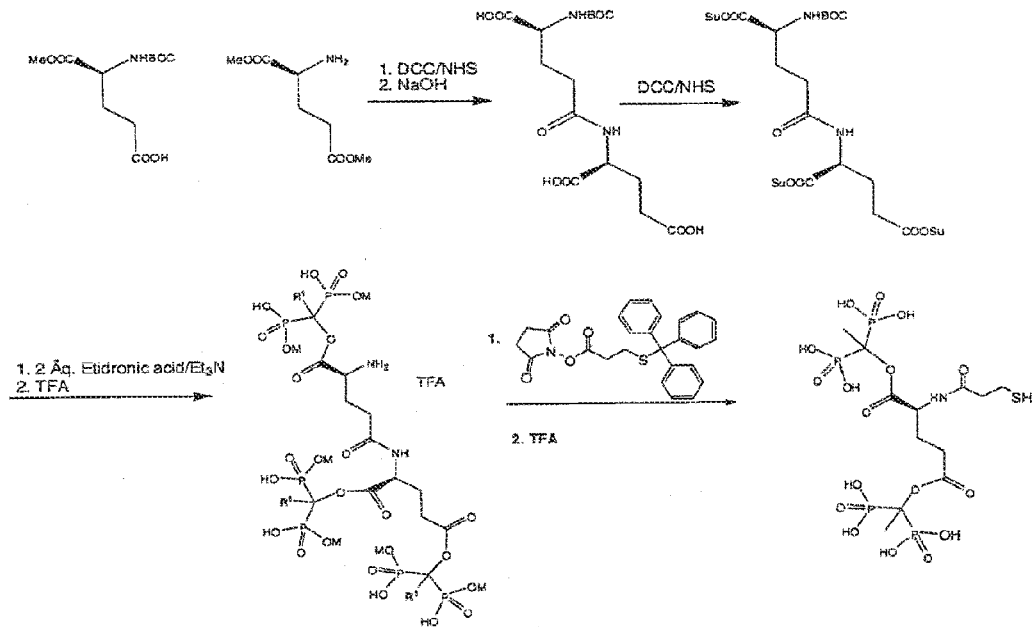

FIG. 9 shows a general scheme of the synthesis of the compound of formula (XXVb).

Figure 10:
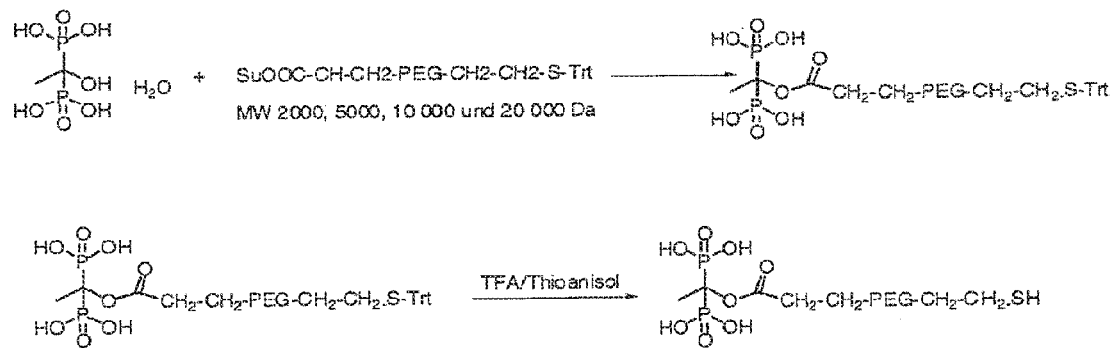

FIG. 10 shows a general scheme of the synthesis of the compound of formula (XXVIb).

According to the present invention, novel target-directed prodrugs are provided which advantageously show an accelerated and specific release of pharmaceutically and/or diagnostically active compounds contained therein when the prodrug is cleaved preferably at the desired site of action. Therefore, a highly improved drug release is advantageously achieved, which is connected to a high efficacy of e.g. a cytostatic treatment of bone disorders such as bone cancer, when compared to the state of the art. Thus, an improved treatment of e.g. bone metastases of a cancer patient is possible, wherein the cytostatic agent contained in the prodrug exhibits less side effects.

The present invention is illustrated in the following examples without any limitations thereto.

To pamidronate (28 mg, 100 µmoL) dissolved in 3 mL 10 mM sodium phosphate buffer containing 1 mM EDTA (pH 7.5) were added EMC-D-Ala-Phe-Lys-Lys-(gamma-MTX)-OH (12.35 mg, 10 µmoL) dissolved in 2.47 mL 10 mM sodium phosphate buffer (pH 5.8). Then iminothiolane (13.7 mg, 100 µmoL dissolved in 1.37 mL in 10 mM sodium phosphate containing 1 mM EDTA (pH 7.5) were added and the solution stirred at room temperature for 4 h.

5 mL of the yellow solution were loaded on a preparative C18-RP-HPLC-column (Macherey-Nagel, 100 Å, Nucleosil 100-7 C18 [21×250 mm] with pre-column) and the product isolated using the following conditions: flow: 10 mL/min; mobile phase A: AcN/10 mM sodium phosphate buffer (10/90, v/v), pH 7.0; mobile phase B: AcN/10 mM sodium phosphate buffer (30/70, v/v), pH 7.0; gradient: 0-5 min 100% mobile phase A; 5-20 min increase to mobile phase B; 20-30 min decrease to initial 100% mobile phase A; 30-40 min isocratic flow with 100% mobile phase A; injection volume: 2 ml; wavelength 370 nm.

The fractions containing the desired product were collected and dried under high vacuum for 24 h (lyophilized) to obtain a light yellow powder. (Yield: ~5 mg, purity 83%).

Analytical HPLC were performed with a Gilson 321 pump, a Kontron 535 detector (at 300 nm) and a Bischoff Lambda 1010 detector (at 370 nm). For peak integration Geminyx software (version 1.91 by Goebel Instrumentelle Analytik) was used; column: Machery-Nagel, 100 Å, Nucleosil 100-5 C18 [4×250 mm] with pre-column; chromatographic conditions: flow: 1.0 mL/min, mobile phase A: AcN/10 mM sodium phosphate buffer (10/90, v/v), pH 7.0; mobile phase B: AcN/10 mM sodium phosphate buffer (30/70, v/v), pH 7.0; gradient: 0-5 min 100% mobile phase A; 5-20 min increase to mobile phase B; 20-30 min decrease to initial 100% mobile phase A; 30-40 min isocratic flow with 100% mobile phase A; injection volume: 50 μL.

EXAMPLE 2

The synthesis of a bisphosphonate prodrug based on a doxorubicin prodrug, the 6-maleimidocaproylhydazone derivative of doxorubicin (DOXO-EMCH) and etidronic acid is described below. DOXO-EMCH is an acid-sensitive thiol-binding drug and it is cleavable at pH 5.0 and releases doxorubicin (F. Kratz et al., *J. Med. Chem.* 2002, 45, 5523-5533).

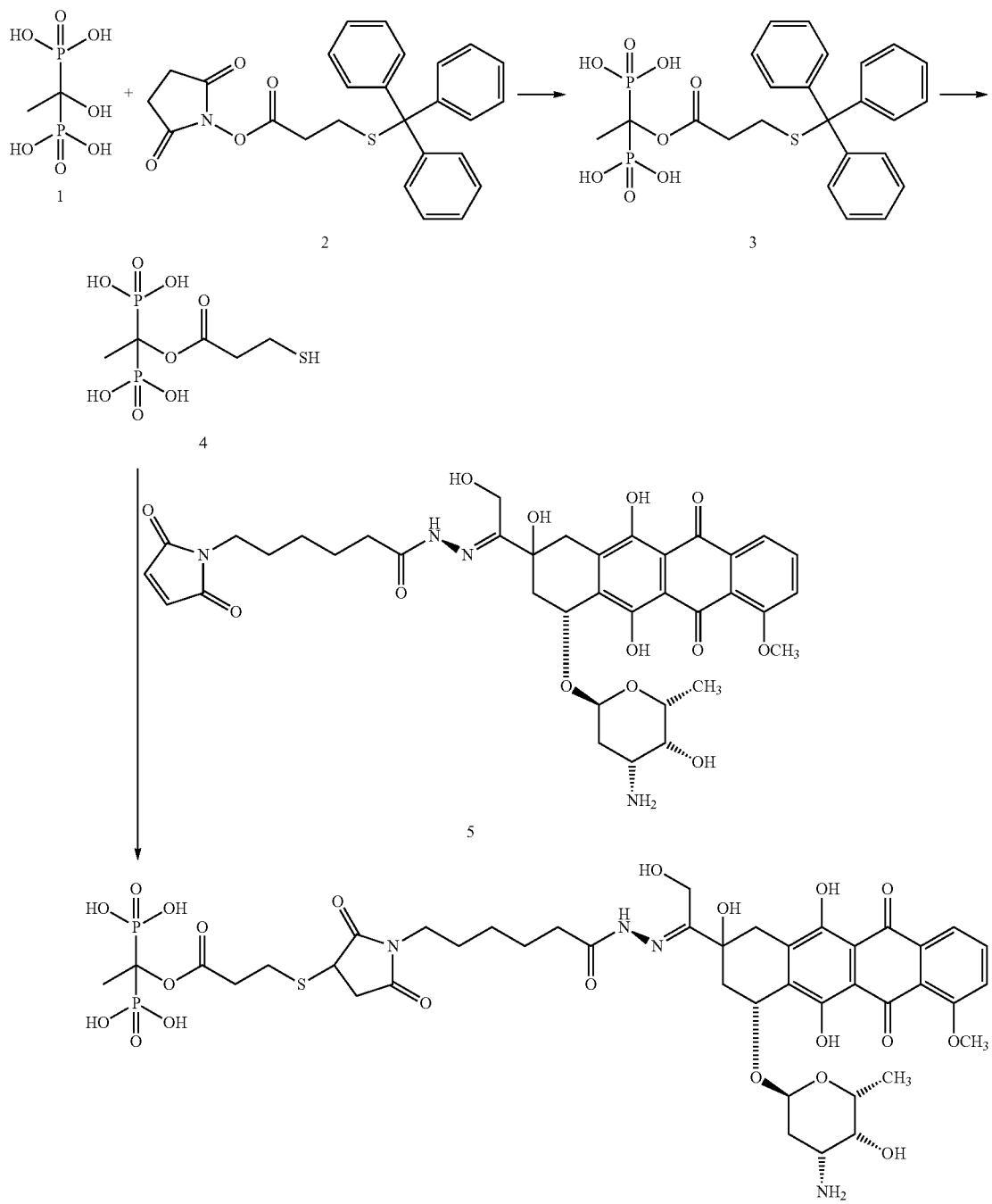

To etidronic acid 1 dissolved in an organic solvent such as tetrahydrofuran or dimethylformamide was added a base (e.g. triethylamine, diisopropylethylamine) and an thiol-protected aliphatic acid. An example of a protected acid is the 3-(tritylthio)propanyloxy-succinimide 2 derivative which was obtained by a reacting 3-(tritylthio)propionic acid with N-hydroxysuccinimide in the presence of dicyclohexylcarbodiimide by crystallization.

The reaction of 1 and (tritylthio)propanyloxy-succinimide 2 was stirred at 65° C. for 48 h. After removing the solvent under reduced pressure, the crude product was purified by C-18 reverse phase HPLC using a mixture of organic and/or aqueous solvent preferably acetonitrile and water or acetonitrile and sodium phosphate buffer as mobile phases to yield the product 3.

The trityl-protecting group was removed conventionally by using a cleavage cocktail containing trifluoroacetic acid, methylene chloride and a scavenger, e.g. triisopropylsilane. The reaction mixture was stirred at room temperature for several hours and the product was precipitated with diethyl ether. After centrifugation the product 4 was dried under high vacuum.

In the next step, DOXO-EMCH 5 dissolved in 10 mM sodium phosphate buffer (pH 5.8) was added to a solution of 4 dissolved in aqueous medium such as 10 mM sodium phosphate buffer (pH 7.0) at 37° C. alternatively using up to 20% of an organic solvent such as tetrahydrofurane, ethanol, methanol or dimethylformamide, and the sample was stirred between 5 min and four hours. The crude product can be purified on a preparative C-18 reverse phase HPLC using acetonitrile/water or acetonitrile/sodium phosphate buffer as mobile phase.

The invention claimed is:

1. A prodrug, comprising general formula (I):

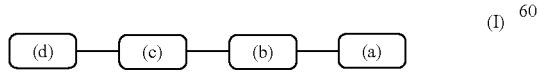

wherein
unit (a) represents a pharmaceutically and/or diagnostically active compound, said pharmaceutically and/or diagnostically active compound is a cytostatic agent selected from the group consisting of N-nitrosoureas, the anthracyclines doxorubicin, 2-pyrollinoanthracycline, morpholinoanthracycline, diacetatoxyalkylanthracycline, daunorubicin, epirubicin, idarubicin, mitoxantrone and ametantrone; the alkylating agents chlorambucil, bendamustine, melphalan, and oxazaphosphorines; the antimetabolites 5-fluorouracil, 2'-deoxy-5-fluorouridine, cytarabine, cladribine, fludarabine, pentostatine, gemcitabine, 6-thioguanine and 6-mercaptopurine; the folic acid antagonists methotrexate, raltitrexed, pemetrexed and plevitrexed; the camptothecins topotecan, irinotecan, SN-38, 10-hydroxycamptothecin, GG211, lurtotecan, 9-aminocamptothecin and camptothecin; the Vinca alkaloids vinblastine, vincristine, vindesine and vinorelbine; calicheamicins; maytansinoids; auristatins; epothilones; duocarmycins; bleomycin, dactinomycin, plicamycin, mitomycin C and cis-configured platinum (II) complexes;

unit (b) represents a cleavable linker which is directly bound to the pharmaceutically and/or diagnostically active compound, said cleavable linker selected from the group consisting of:

(i) an enzymatically cleavable peptide sequence selected from the group consisting of -Arg-, -Arg-Arg-, -Phe-Arg-, -Phe-Cit-, -Ile-Pro-Lys-, -Lys-, -Lys-Lys-, -Arg-Lys-, -Leu-Arg-, -Phe-Arg-, -Val-Arg-, -Ala-Leu-Ala-Leu- [SEQ ID NO:1], -Phe-Lys-, -Phe-Lys-Ala-, -Val-Cit-, -Val-Ala-, -Val-Arg-, -Ala-Phe-Lys-, -D-Ala-Phe-Lys-, -Ser-Ser-Tyr-Tyr-Ser-Arg- [SEQ ID NO:2], -Phe-Pro-Lys-Phe-Phe-Ser-Arg-Gln- [SEQ ID NO:3], -Lys-Pro-Ile-Glu-Phe-Nph-Arg-Leu- [SEQ ID NO:4], -Gly-Pro-Leu-Gly-Ile-Ala-Gly-Gln- [SEQ ID NO:5], -Gly-Pro-Gln-Gly-Ile-Trp-Gly-Gln- [SEQ ID NO:6], -Gly-Phe-Leu-Gly- [SEQ ID NO:7], -Gly-Gly-, -Gly-Gly-Gly- and -Gly-Gly-Gly-Arg-Arg- [SEQ ID NO:8]

(ii) an acid-sensitive group which can be cleaved upon a decrease in the pH-value and which is selected from the croup consisting of ester, acetal, ketal, imine, hydrazone, acylhydrazone and sulfonylhydrazone bonds or bonds containing a trityl group;

(iii) the enzymatically cleavable peptide sequence of (i) bound to a self-immolative croup which is selected from the croup consisting of:

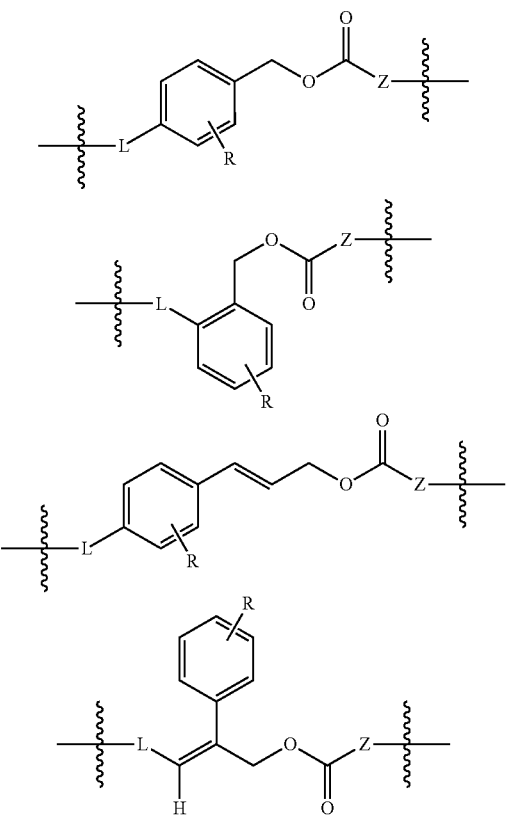

-continued

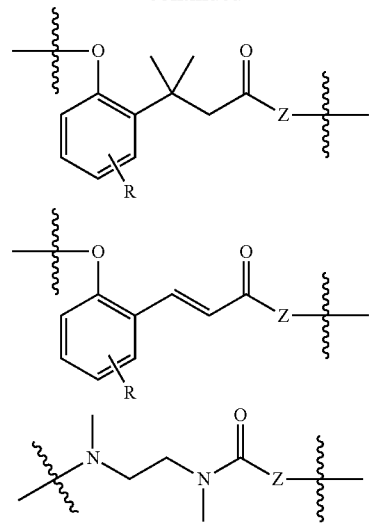

wherein the pharmaceutically and/or diagnostically active compound (a) is bound to the Z-terminus of the self-immolative group, wherein L and Z are independently selected from O, S and NH, and R represents one or more substituents at the phenyl ring which are independently selected from the group consisting of F, Cl, Br, I, $NO_2$, CN, OH, a $C_{1-8}$ alkyl group and a $C_{1-6}$ aryl group; or (iv) the acid-sensitive group of (iii) bound to a self-immolative group which is selected from the group consisting of:

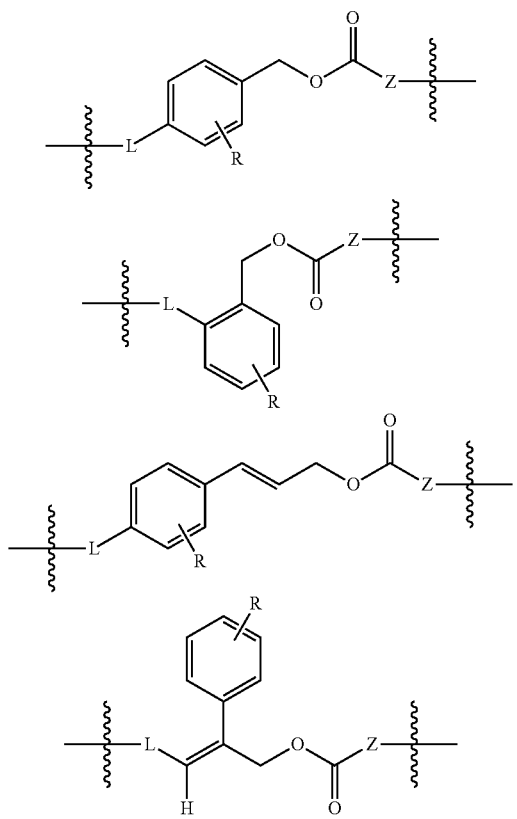

-continued

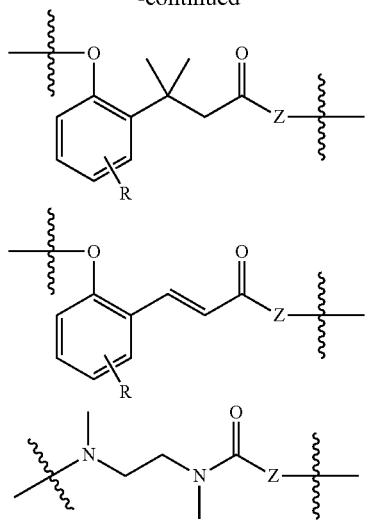

wherein the pharmaceutically and/or diagnostically active compound (a) is bound to the Z-terminus of the self-immolative group, wherein L and Z are independently selected from O, S and NH, and R represents one or more substituents at the phenyl ring which are independently selected from the group consisting of F, Cl, Br, I, $NO_2$, CN, OH, a $C_{1-8}$ alkyl group and a $C_{1-6}$ aryl group;

unit (c) represents a spacer group which is directly bound to the cleavable linker, the spacer group selected from the group consisting of a maleinimide—obtained unit, a halogenacetamide—obtained unit, a halogenacetate—obtained unit, a pyridylthio—obtained unit, a vinyl carbonyl—obtained unit, an aziridin—obtained unit, a disulfide—obtained unit, and a substituted or unsubstituted acetylene—obtained unit; and unit (d) represents one or more bisphosphonate groups which are directly bound to the spacer group, the one or more bisphosphonate groups are independently selected from the group consisting of etidronate, clodronate, tiludronate, pamidronate, 1-amino-1,1-diphosphonate methane, risedronate, ibandronate, 1-hydroxy ethylidene-1,1-diphosphonic acid, alendronate and zoledronate, or wherein the one of more bisphosphonate groups (d) are independently one of the following structures (IIa) to (Va), (IIb) to (Vb), (VIa) to (VIIIa) or (VIb) to (VIIIb):

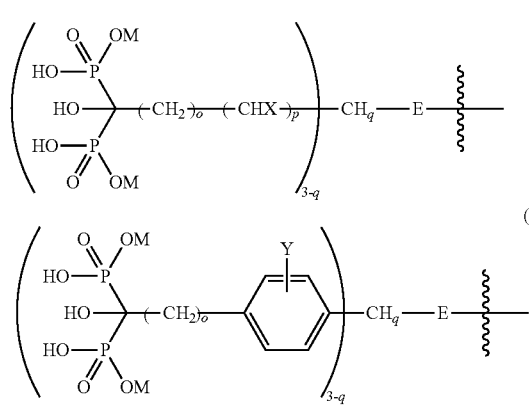

(IIa)

(IIIa)

-continued

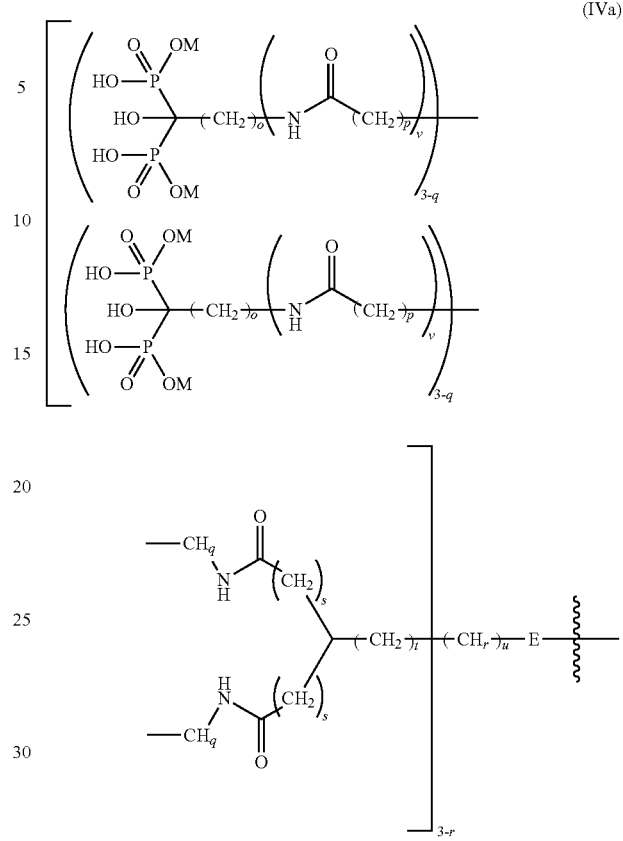

(IVa)

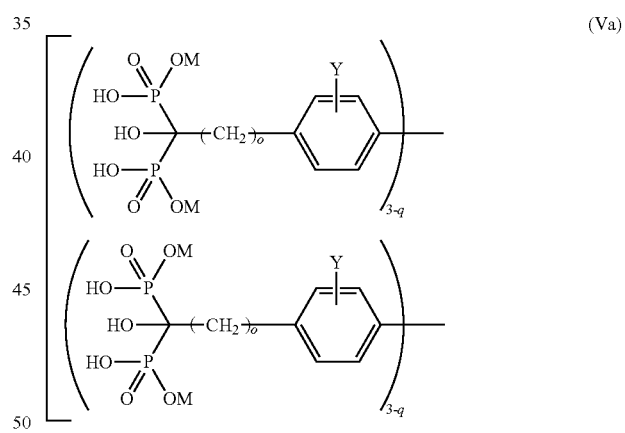

(Va)

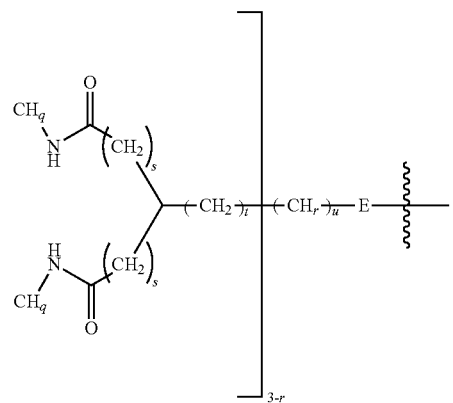

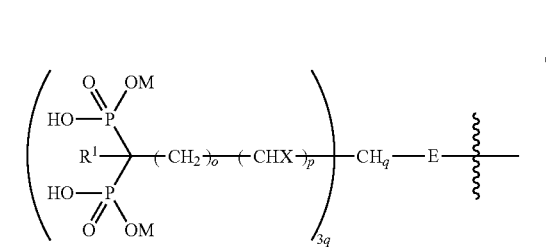
(IIb)
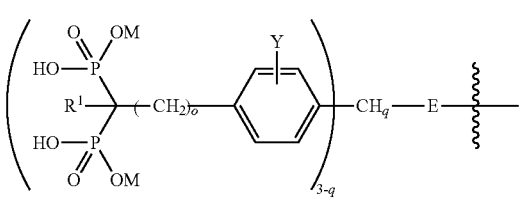
(IIIb)
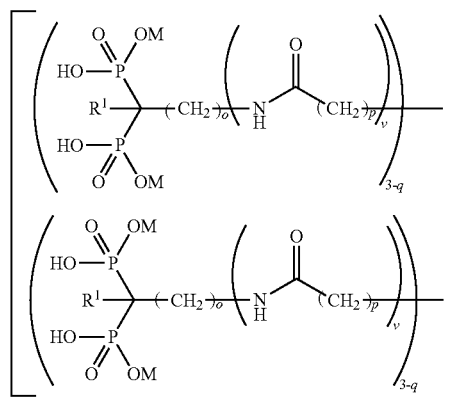
(IVb)
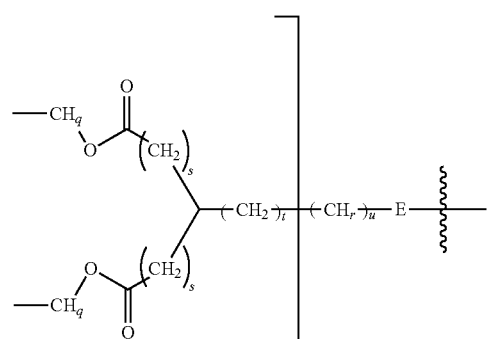
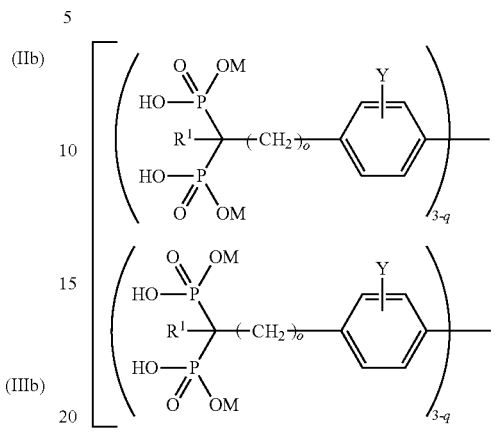
(Vb)
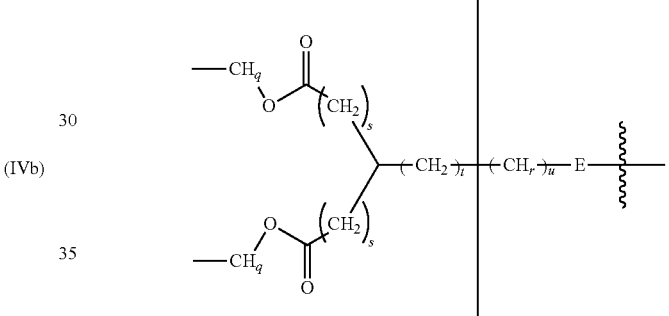
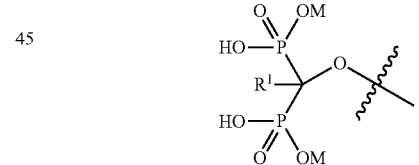
(VIb)
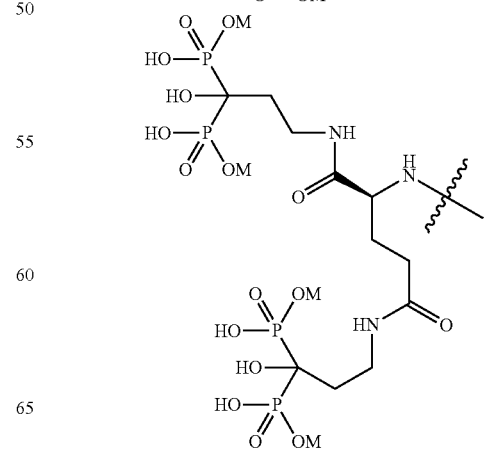
(VIIa)

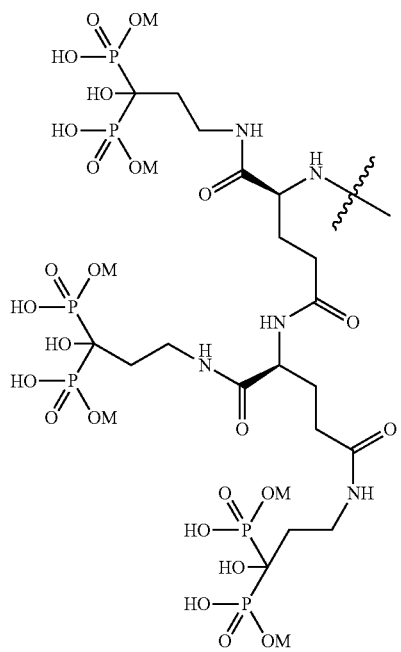

(VIIIa)

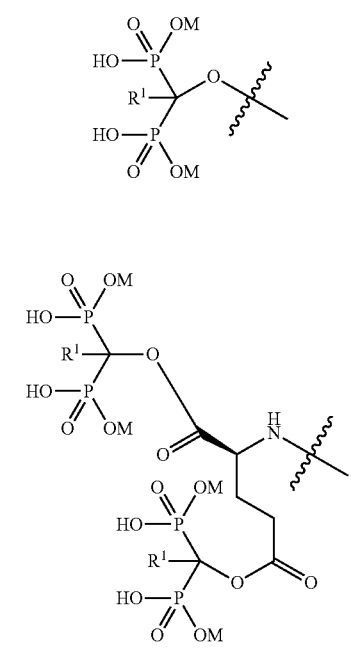

(VIb)

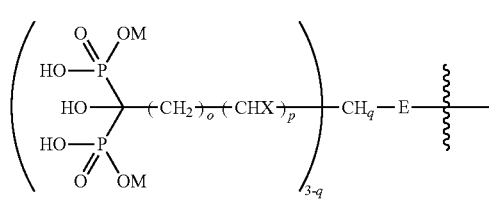

(VIIb)

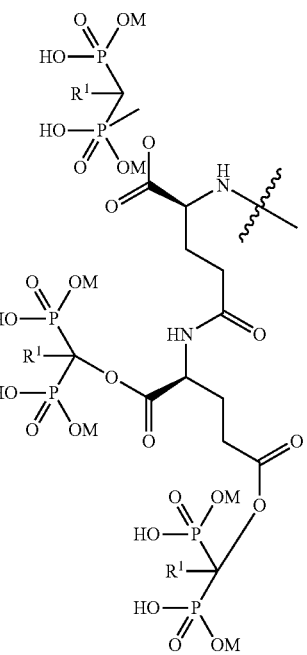

(VIIIb)

wherein
o is an integer independently selected from 0 to 12,
p is an integer independently selected from 0 to 2,
q is an integer independently selected from 0 to 2,
r is an integer independently selected from 1 or 2,
s is an integer independently selected from 0 to 12,
t is an integer independently selected from 0 to 2,
u is an integer independently selected from 0 or 1,
v is an integer independently selected from 0 to 2,
each of X and Y are independently selected from the group consisting of F, Cl, Br, I, $NO_2$, $SO_3H$, CN, OH, COOH, $COOCH_3$, —CHO, —$CHOCH_3$, an $C_{1-8}$ alkyl group and an $C_{1-6}$ aryl group,
$R^1$ is the same or different and is independently selected from the group consisting of F, Cl, Br, I, $NO_2$, CN, $COOCH_3$, —CHO, —$CHOCH_3$, an $C_{1-8}$ alkyl group and an $C_{1-6}$ aryl group,
E represents O, NH, a carbon-carbon single bond, a carbon-carbon double bond or a carbon-carbon triple bond, and
M is independently selected from hydrogen, sodium, potassium, calcium and magnesium.

2. The prodrug according to claim 1, wherein an aliphatic chain —$(CH_2)_n$— is bound to the spacer group (c) with n being an integer of from 1 to 12, an oligoethylene glycol —$(O-CH_2-CH_2)_n$— with n being an integer of from 1 to 12, or a phenyl ring, optionally substituted with one or more substituents selected from the group consisting of F, Cl, Br, I, $NO_2$, $SO_3H$, CN, OH, COOH, a $C_{1-8}$ alkyl group and a $C_{1-6}$ aryl group, or combinations thereof.

3. The prodrug according to claim 1, wherein the unit (d) represents the one or more bisphosphonate groups having one of the following structures (IIa) to (Va) or (IIb) to (Vb):

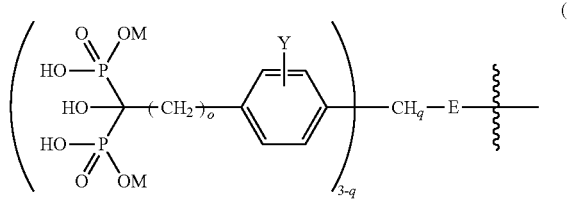

-continued
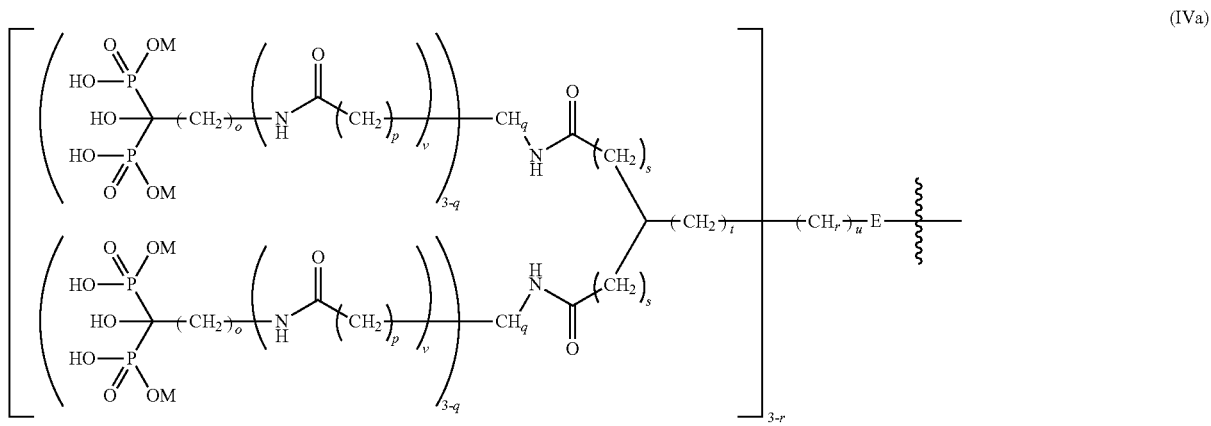
(IVa)
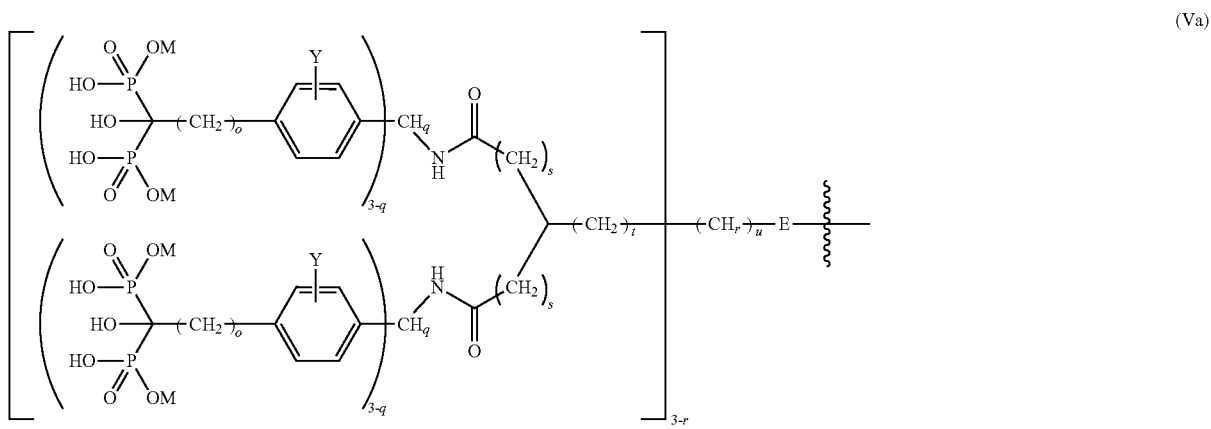
(Va)
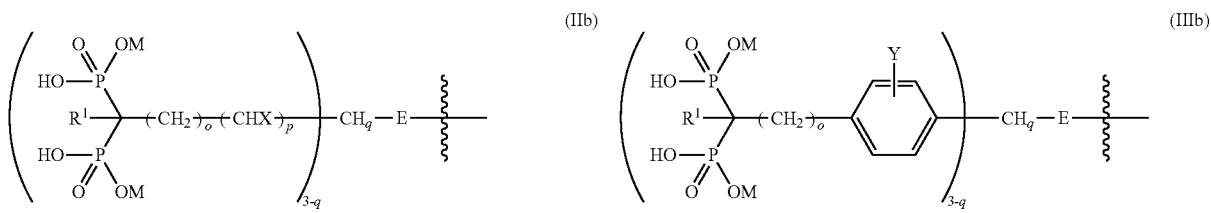
(IIb) (IIIb)
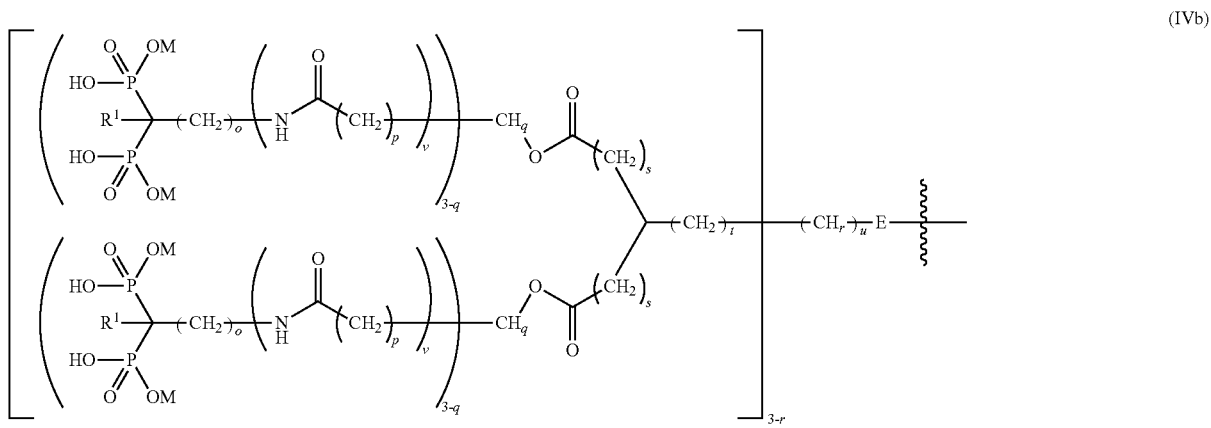
(IVb)

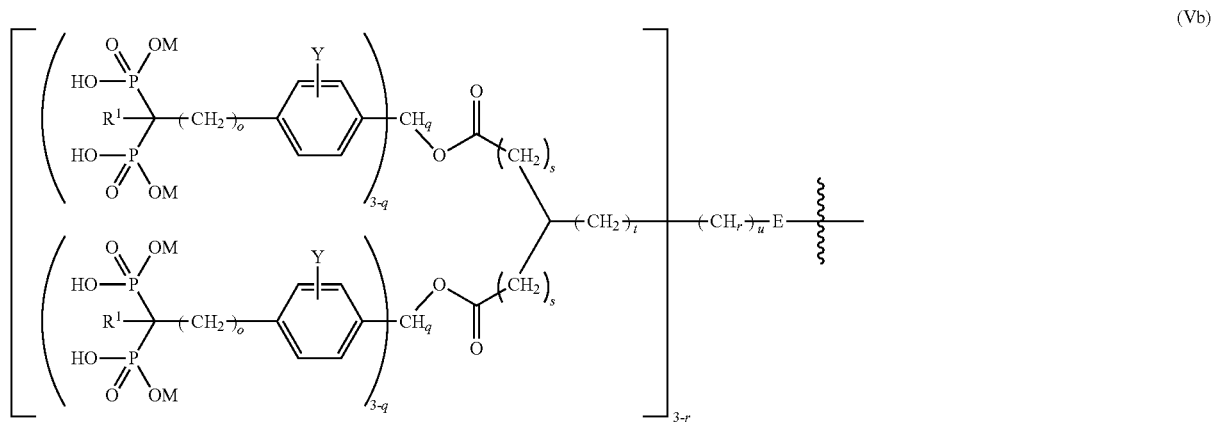
wherein o, p, q, r, s, t, u, v, X, Y, R¹, E and M are as defined above.
4. The prodrug according to claim 1, wherein the unit (d) is selected from one of the following structures (VIa) to (VIIIa) or (VIb) to (VIIIb)
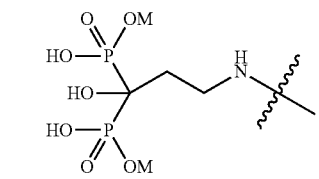
(VIa)
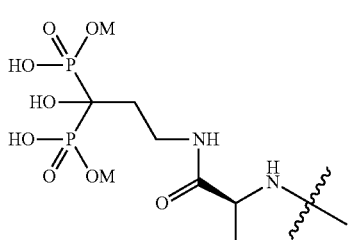
(VIIa)
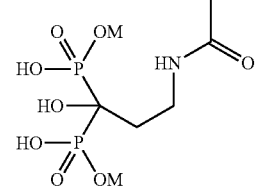
(VIb)
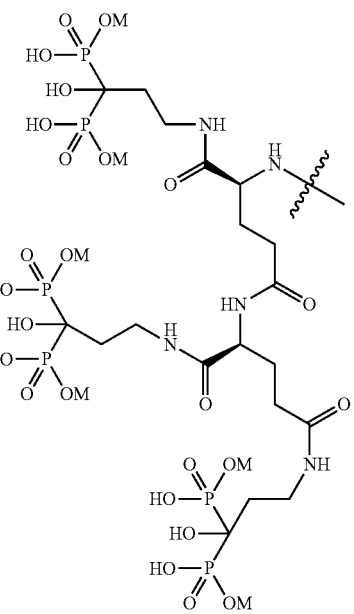
(VIIIa)

-continued

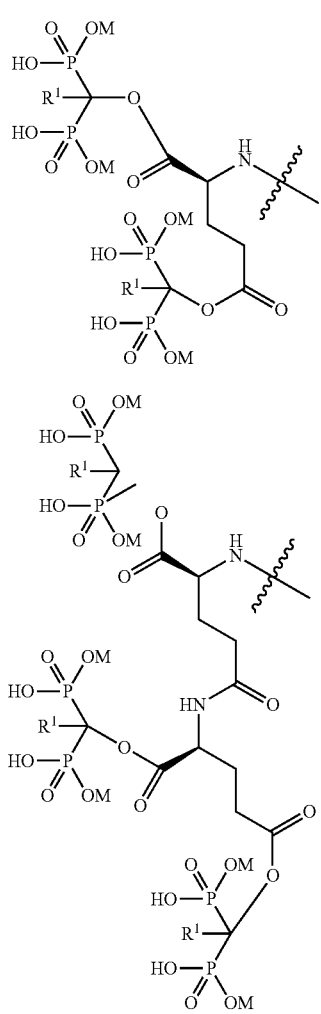

(VIIb)

(VIIIb)

wherein

R¹ may be the same or different and is independently selected from the group consisting of F, Cl, Br, I, NO₂, CN, COOCH₃, —CHO, —CHOCH₃, an $C_{1-8}$ alkyl group and an $C_{1-6}$ aryl group, and M is independently selected from hydrogen, sodium, potassium, calcium and magnesium.

5. The prodrug according to claim 3, wherein the unit (c) is selected from one of the following structures (IX) to (XII):

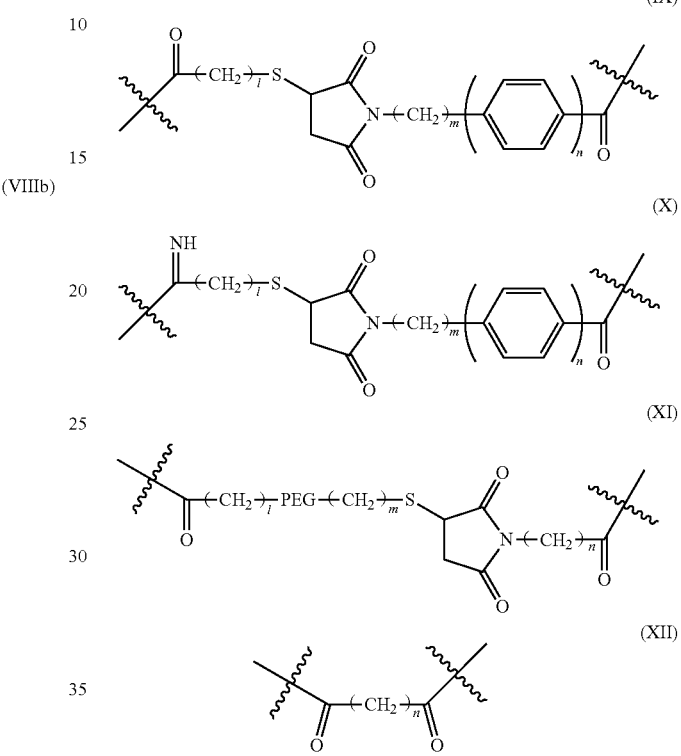

(IX)

(X)

(XI)

(XII)

wherein PEG represents polyethylene glycol), and l, m and n are independently selected from an integer of from 0 to 12.

6. The prodrug according to claim 3, wherein the units (a) and (b) taken together are selected from one of the following structures (XIII) to (XVII):

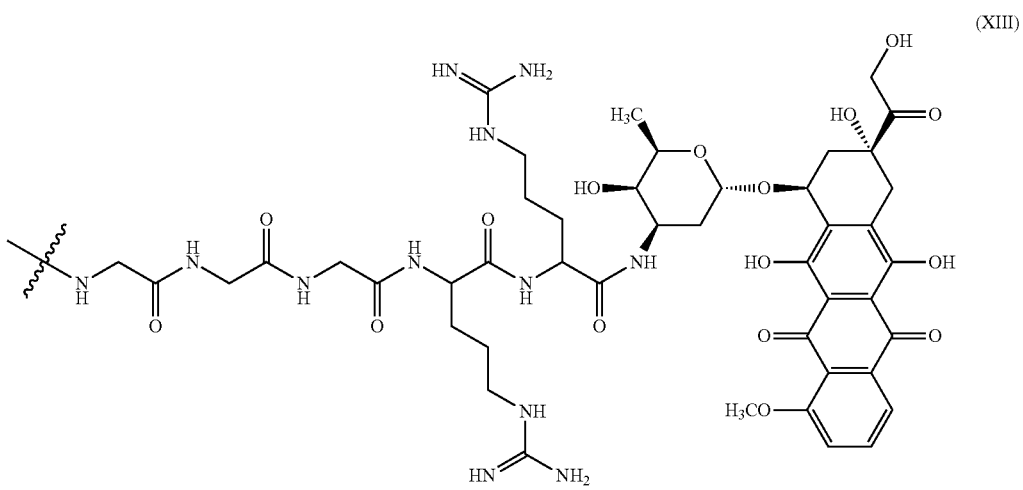

(XIII)

-continued
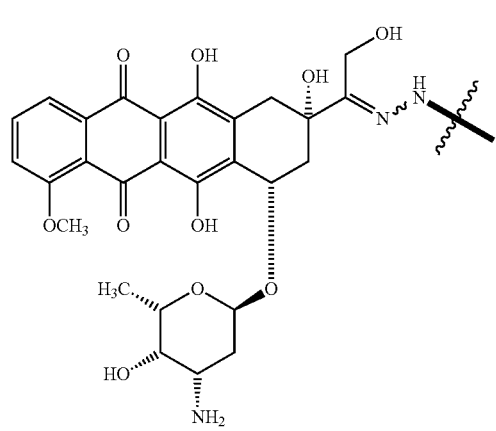
(XIV)
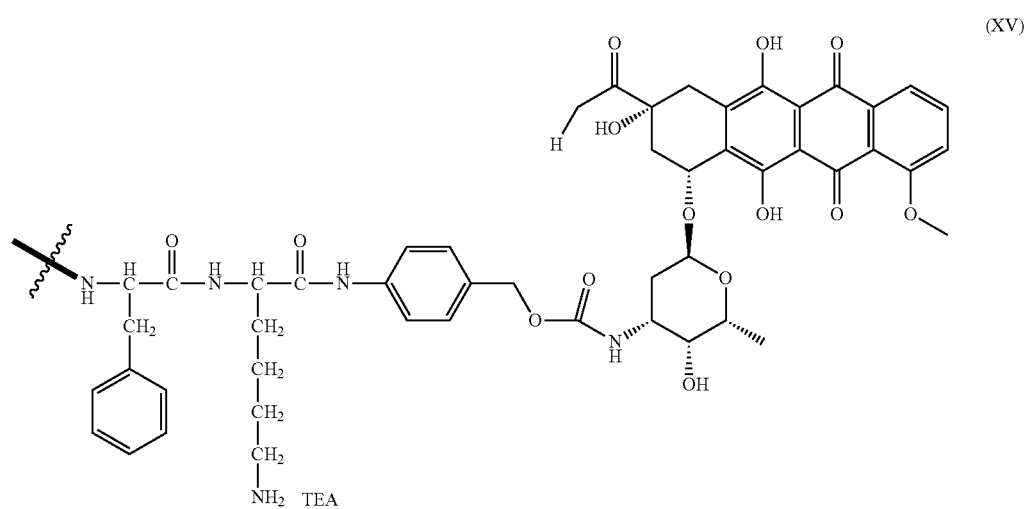
(XV)
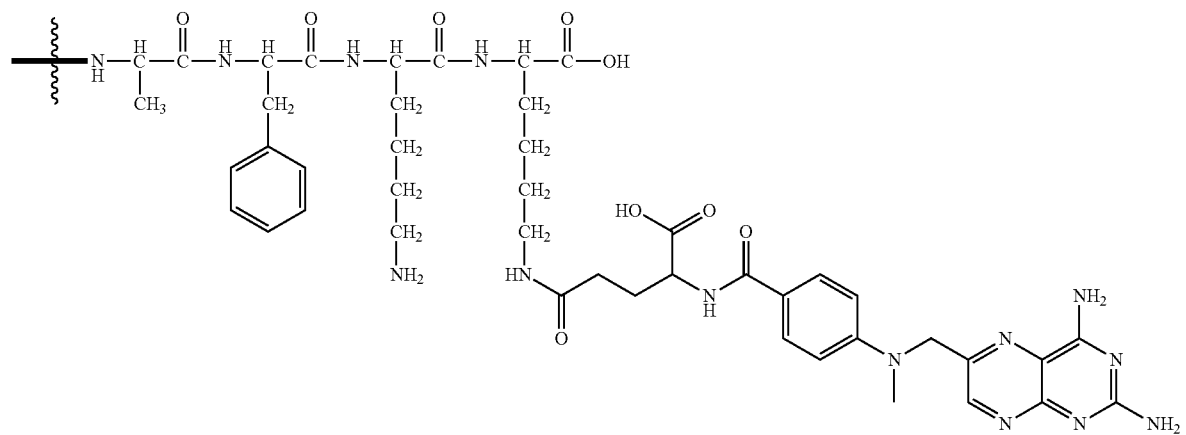
(XVI)

-continued
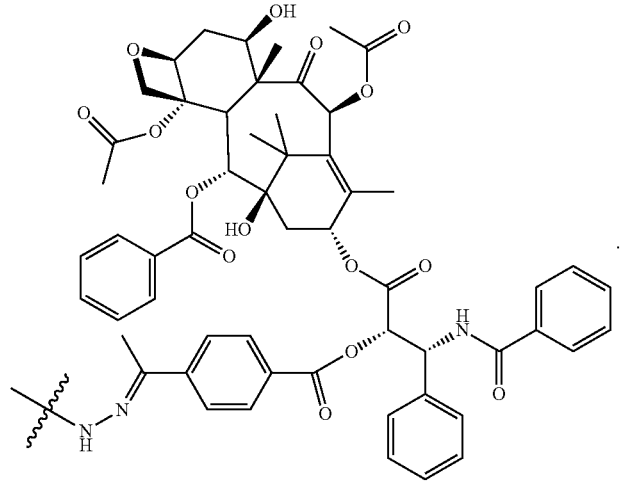
(XVII)
7. A pharmaceutical composition comprising the prodrug according to claim 1, and optionally a pharmaceutically acceptable carrier, a pharmaceutically acceptable adjuvant and/or a diluent.
8. A prodrug of formula (6):
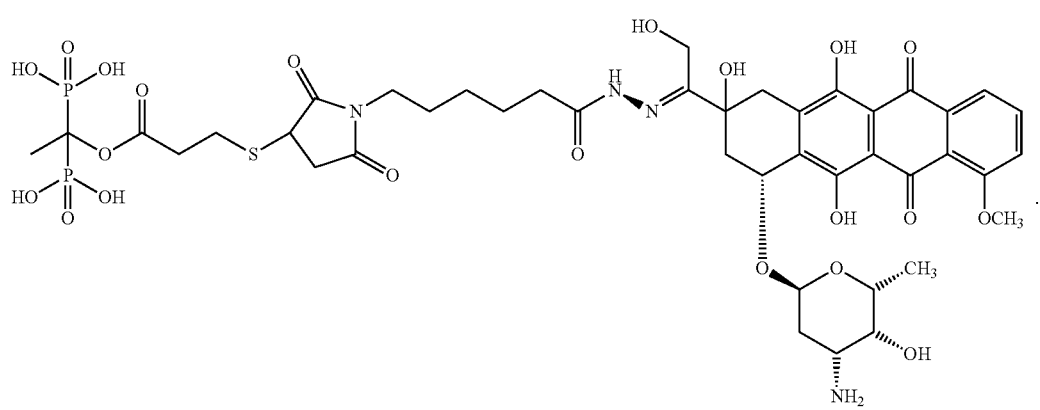
(6)
* * * * *